United States Patent
Woo et al.

(10) Patent No.: US 8,916,708 B2
(45) Date of Patent: *Dec. 23, 2014

(54) UREA DERIVATIVES AND THEIR THERAPEUTIC USE IN THE TREATMENT OF, INTER ALIA, DISEASES OF THE RESPIRATORY TRACT

(75) Inventors: Chi-kit Woo, Harlow (GB); Monique Bodil Van Niel, Harlow (GB)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/701,989

(22) PCT Filed: Jun. 9, 2011

(86) PCT No.: PCT/GB2011/051076
§ 371 (c)(1),
(2), (4) Date: Feb. 15, 2013

(87) PCT Pub. No.: WO2011/154738
PCT Pub. Date: Dec. 15, 2011

(65) Prior Publication Data
US 2013/0143914 A1  Jun. 6, 2013

(30) Foreign Application Priority Data
Jun. 10, 2010  (GB) .................................. 1009731.9

(51) Int. Cl.
*C07D 221/02*  (2006.01)
*A61K 31/44*  (2006.01)
*C07D 471/04*  (2006.01)
*C07D 401/12*  (2006.01)

(52) U.S. Cl.
CPC ............ *C07D 471/04* (2013.01); *C07D 401/12* (2013.01)
USPC .......................................... 546/112; 514/303

(58) Field of Classification Search
None
See application file for complete search history.

(56) References Cited

U.S. PATENT DOCUMENTS

| 2009/0012079 A1 | 1/2009 | Lewthwaite et al. |
| 2012/0088763 A1 | 4/2012 | Finch et al. |

FOREIGN PATENT DOCUMENTS

| CN | 101006087 A | 7/2007 |
| WO | 02 092576 | 11/2002 |
| WO | 2007 091152 | 8/2007 |

OTHER PUBLICATIONS

U.S. Appl. No. 13/708,324, filed Dec. 7, 2012, Van Niel, et al.
U.S. Appl. No. 13/708,191, filed Dec. 7, 2012, Van Niel, et al.
International Search Report Issued Oct. 13, 2011 in PCT/GB11/051076 Filed Jun. 9, 2011.
Office Action issued in corresponding Chinese patent application No. 201180026836.3 dated Aug. 29, 2014 (with English translation).
Sarma et al—"3D-QSAR (Quantitative Structure-Activity Relationships) Studies on Urea Derivatives as Inhibitors of p38 MAP Kinase", Internet Electronic Journal of Molecular Design, Feb. 2008, vol. 7, No. 2, pp. 38-46.

*Primary Examiner* — Heidi Reese
(74) *Attorney, Agent, or Firm* — Oblon, Spivak, McClelland, Maier & Neustadt, L.L.P.

(57) ABSTRACT

Compounds of formula (I) are p38 MAPK inhibitors, useful as anti-inflammatory agents in the treatment of, inter alia, diseases of the respiratory wherein $R^1$ is a radical of formula (IA) or (IB) or (IC): 10 Y is —O— or —S(O)$_p$—wherein p is 0, 1 or 2; A is an optionally substituted cycloalkylene radical having 5, 6 or 7 ring atoms fused to a phenyl ring; and $R^2$, R3b and R4b are as defined in the claims.

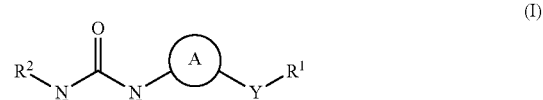

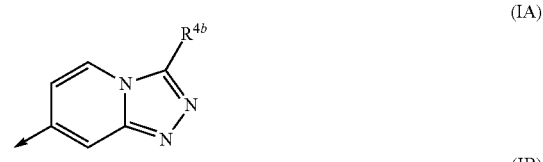

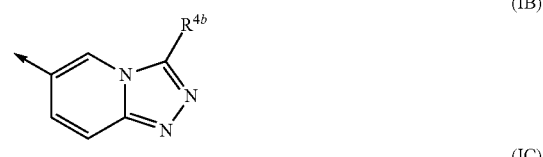

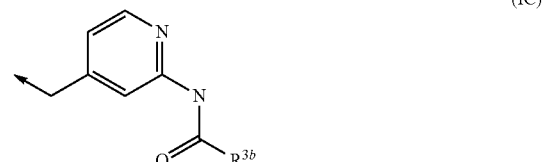

8 Claims, No Drawings

UREA DERIVATIVES AND THEIR THERAPEUTIC USE IN THE TREATMENT OF, INTER ALIA, DISEASES OF THE RESPIRATORY TRACT

CROSS REFERENCES TO RELATED APPLICATIONS

This application is a 371 of International Patent Application No. PCT/GB2011/051076, filed on June 9, 2011, and claims priority to GB Patent Application No. 1009731.9, filed on June 10, 2011, both of which are incorporated herein by reference in their entireties.

FIELD OF THE INVENTION

This invention relates to compounds and compositions that are p38 MAPK inhibitors, useful as anti-inflammatory agents in the treatment of, inter alia, diseases of the respiratory tract.

BACKGROUND TO THE INVENTION

Mitogen activated protein kinases (MAPK) constitute a family of proline-directed serine/threonine kinases that activate their substrates by dual phosphorylation. There are four known human isoforms of p38 MAP kinase, p38α, p38β, p38γ and p38δ. The p38 kinases, which are also known as cytokine suppressive anti-inflammatory drug binding proteins (CSBP), stress activated protein kinases (SAP K) and RK, are responsible for phosphorylating (Stein et al., Ann. Rep. Med. Chem., 1996, 31, 289-298) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (Herlaar E. & Brown Z., Molecular Medicine Today, 1999, 5, 439-447). The products of p38 phosphorylation have been shown to mediate the production of inflammatory cytokines, including tumor necrosis factor alpha (TNF α) and interleukin-(IL-)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (e.g. Dinarello et al., Rev. Infect. Disease, 1984, 6, 51). Excessive or unregulated TNF production (particularly TNF☐) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (Badger et al., J. Pharm, Exp. Thera., 1996, 279, 1453-1461; Griswold et al, Pharmacol. Comm., 1996, 7, 323-229). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-αIL-1β, IL-6, IL-4, IL-5 and IL-13 (Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (Lee et al., Immunopharmacology, 2000, 47, 185-200). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425). It is believed that the compounds of the present invention can be used to treat p38 mediated diseases such as: asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemaginomas, angiofibroma of the nasopharynx, and avascular necrosis of bone, benign and malignant tumors/neoplasia including cancer, leukaemia, lymphoma, systemic lupus erthrematosis (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467). P38 kinase inhibitors containing a triazolopyridine motif are known in the art, for example WO07/091,152, WO04/072072, WO06/018727.

BRIEF DESCRIPTION OF THE INVENTION

The compounds of the present invention are inhibitors of p38 mitogen activated protein kinase ("p38 MAPK", "p38 kinase" or "p38"), including p38a kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

DESCRIPTION OF THE INVENTION

According to the invention there is provided compound of formula (I), or a pharmaceutically acceptable salt thereof:

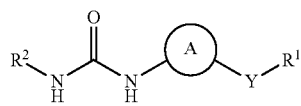
(I)

wherein;

$R^1$ is a radical of formula (IA) or (IB) or (IC):

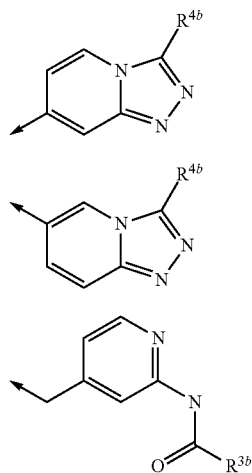

wherein $R^{4b}$ is $C_1$-$C_6$ alkyl, $C_3$-$C_6$ cycloalkyl, phenyl which is optionally substituted, 5- or 6-membered monocyclic heteroaryl which is optionally substituted or a radical of formula (IIa) or (IIb)

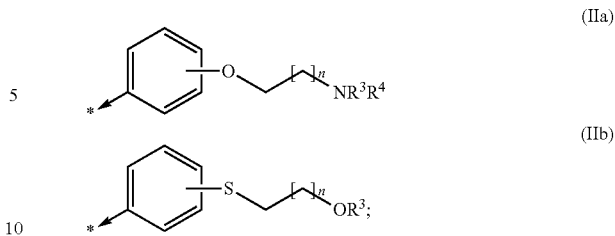

wherein n is 1 or 2; and $R^3$ and $R^4$ are independently H or $C_1$-$C_6$ alkyl, or $R^3$ and $R^4$ taken together with the nitrogen to which they are attached form a 6-membered heterocyclic ring optionally containing a further heteroatom selected from N and O;

$R^{3b}$ is optionally substituted $C_1$-$C_6$ alkyl; —$NH_2$; mono- or di-($C_1$-$C_6$) alkylamino; mono- or di-($C_1$-$C_3$) alkyl-X—($C_1$-$C_3$)alkylamino wherein X is O, S or NH; N-morpholino; N-piperidinyl, N-piperazinyl or N—($C_1$-$C_3$)alkylpiperazin-1-yl;

Y is —O— or —S(O)$_p$— wherein p is 0, 1 or 2;

A is an optionally substituted cycloalkylene radical having 5, 6 or 7 ring atoms fused to a phenyl ring;

$R^2$ is a radical of formula (IIIa), (IIIb), (IIIc), (IIId) or (IIIe):

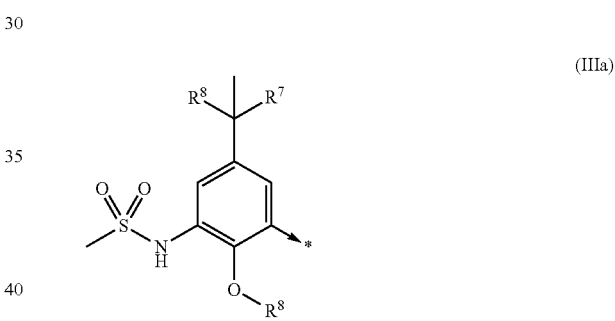

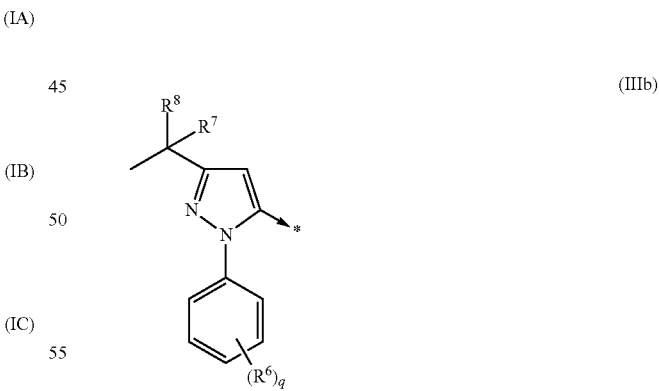

-continued

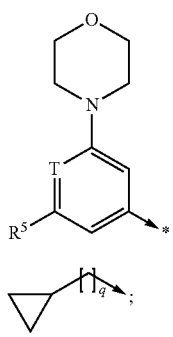
(IIId)

(IIIe)

wherein
q is 0, 1, 2 or 3;
T is —N= or —CH=;
$R^5$ is H or F;0
$R^7$ is —CH$_3$; —C$_2$H$_5$—CH$_2$OH, —CH$_2$SCH$_3$—SCH$_3$ or —SC$_2$H$_5$;
$R^8$ is —CH$_3$ or —C$_2$H$_5$ and
each occurrence of $R^6$ is independently H, C$_1$-C$_6$ alkyl, hydroxy or halo; or a single occurrence of $R^6$ is a radical of formula (IVa), (IVb) or (IVc)

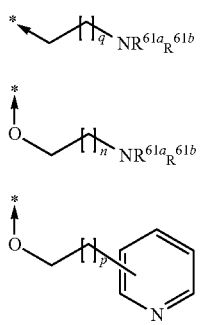

(IVa)

(IVb)

(IVc)

while any other occurrence of $R^6$ is independently H, C$_1$-C$_6$ alkyl, hydroxyl or halo;
wherein in formulae (IVa), (IVb) and (IVc) n and p are as defined above; and wherein in $R^6$
$R^{61a}$ and $R^{61b}$ are H, alkyl, or $R^{61a}$ and $R^{61b}$ may be joined together with the nitrogen to which they are attached to form a 4-7 membered heterocyclic ring optionally containing a further heteroatom selected from N and O, such as a piperidine, piperazine or morpholine ring.

In another aspect, the invention includes pharmaceutical compositions comprising a compound of the invention, together with one or more pharmaceutically acceptable carriers and/or excipients. Particularly preferred are compositions adapted for inhalation for pulmonary administration.

In another aspect, the invention includes the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, broncietasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

Terminology

As used herein, the term "(C$_a$-C$_b$)alkyl" wherein a and b are integers, refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein, the term "carbocyclic" refers to a mono-, bi- or tricyclic radical having up to 16 ring atoms, all of which are carbon, and includes aryl and cycloalkyl.

As used herein, the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

The term "divalent cycloalkylene radical" refers to a cycloalkyl radical having two unsatisfied valencies such as 1,3-cyclopentylene, 1,4-cyclohexylene and 1,4-cycloheptylene as follows:

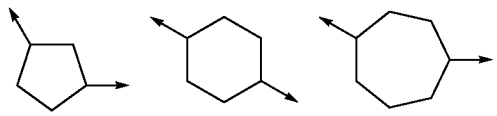

As used herein, the unqualified term "aryl" refers to a mono- or bi-cyclic carbocyclic aromatic radical, and includes radicals having two monocyclic carbocyclic aromatic rings which are directly linked by a covalent bond. Illustrative of such radicals are phenyl, biphenyl and napthyl.

As used herein, the unqualified term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative examples of such radicals are thienyl, benzothienyl, furyl, benzofuryl, pyrrolyl, imidazolyl, benzimidazolyl, thiazolyl, benzothiazolyl, isothiazolyl, benzisothiazolyl, pyrazolyl, oxazolyl, benzoxazolyl, isoxazolyl, benzisoxazolyl, isothiazolyl, triazolyl, benzotriazolyl, thiadiazolyl, oxadiazolyl, pyridinyl, pyridazinyl, pyrimidinyl, pyrazinyl, triazinyl, indolyl and indazolyl.

As used herein, the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any aryl or heteroaryl moiety herein means substituted with at least one substituent, for example selected from $(C_1-C_6)$ alkyl, $(C_1-C_6)$ fluoroalkyl, $(C_1-C_6)$ alkoxy (including methylenedioxy and ethylenedioxy substitution on adjacent carbon atoms of an aromatic ring), $(C_1-C_6)$fluoroalkoxy, $(C_1-C_6)$alkoxy-$(C_1-C_6)$ alkyl, benzyloxy-$(C_1-C_6)$alkyl, $(C_1-C_6)$alkoxy-$(C_1-C_6)$ alkoxy, benzyloxy-$(C_1-C_6)$alkoxy, hydroxy, hydroxy$(C_1-C_6)$ alkyl, hydroxy$(C_1-C_6)$alkoxy, hydroxy$(C_1-C_6)$alkylthio, mercapto, mercapto$(C_1-C_6)$alkyl, $(C_1-C_6)$alkylthio, cyclopropyl, halo (including fluoro and chloro), O-benzyl, nitro, nitrile (cyano), —COOH, tetrazolyl, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_4)$alkyl group, or R$^A$ and R$^B$ when attached to the same nitrogen may form, together with that nitrogen, a cyclic amino group such as a morpholinyl, piperidinyl or piperazinyl group. An "optional substituent" may be one of the substituent groups encompassed in the above description.

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

As used herein the term "salt" includes base addition, acid addition and ammonium salts. As briefly mentioned above compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds (I) which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalenebis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002).

It is expected that compounds of the invention may be prepared in the is form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal habits.

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-druqs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, in Textbook of Drug Design and Discovery, 3$^{rd}$ Edition, 2002, Taylor and Francis).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985). Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

Embodiments of the Invention

In some embodiments of the invention R$^1$ is a radical of formula (IA) or (IB). Of those radicals, formula (IB) is currently preferred. In radicals (IA) or (IB):

R$^{4b}$ may be C$_1$-C$_6$ alkyl, such as an isopropyl group;

R$^{4b}$ may be C$_3$-C$_6$ cycloalkyl, such as cyclopentyl;

R$^{4b}$ may a be phenyl; more especially the phenyl group is substituted by one or two groups selected from C$_1$-C$_6$ alkyl, halogen (for example chloro) or hydroxy; for example the phenyl group may be substituted in the 2- and/or 6-position; specifically, R$^{4b}$ may be 2,6-dichlorophenyl, 2-chlorophenyl, or 2-hydroxyphenyl;

R$^{4b}$ may be a group of formula (IIa) or a group of formula (IIb);

In other embodiments of the invention R$^1$ is a radical of formula (IC). In the radical or formula (IC):

R$^{3b}$ may be C$_1$-C$_6$ alkyl, such as C$_1$-C$_3$ alkyl, examples being methyl, ethyl, n- or iso-propyl. R$^{3b}$ may be substituted C$_1$-C$_6$ alkyl, such as substituted C$_1$-C$_3$ alkyl, said substituents being defined above. Examples of such substituents include C$_1$-C$_6$ alkoxy, C$_1$-C$_6$ alkylsulfonyl, A preferred group R$^{3b}$ is methoxymethyl.

R$^{3b}$ may also be —NH$_2$; mono- or di-(C$_1$-C$_6$) alkylamino; mono- or di-(C$_1$-C$_3$) alkyl-X—(C$_1$-C$_3$) alkyl amino wherein X is O, S or NH; N-morpholino; N-piperidinyl, N-piperazinyl or N—(C$_1$-C$_3$)alkylpiperazin-1-yl;

The Linker Y

Y is —O— or —S(O)$_p$—. For example Y may be —O— or —S—. At present it is preferred that Y be —O—;

The Group A

A may be, for example a divalent radical of formula (Va) in either orientation;

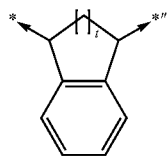

(Va)

wherein t is 1, 2 or 3.

The —N(H)-A-Y— radical may be a divalent radical having one of the stereospecific formulae (B), (C), (D), (E), (F), (G), (H), (I) or (J), wherein Y is as defined with reference to formula (I):

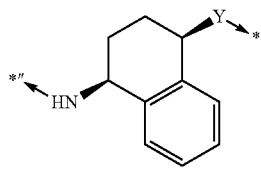

(B)

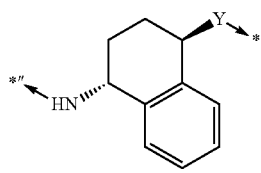

(C)

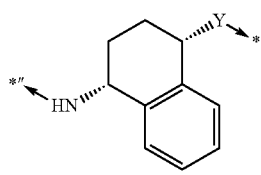

(D)

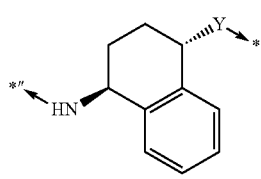

(E)

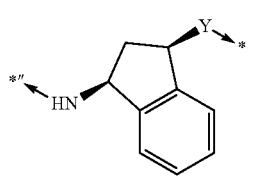

(F)

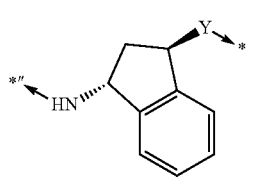

(G)

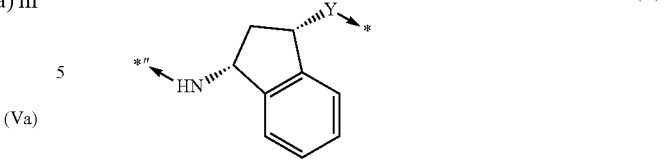

(H)

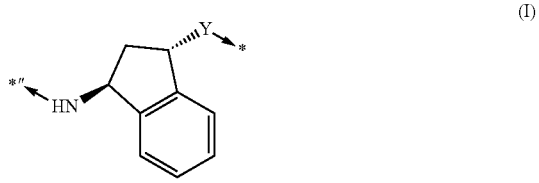

(I)

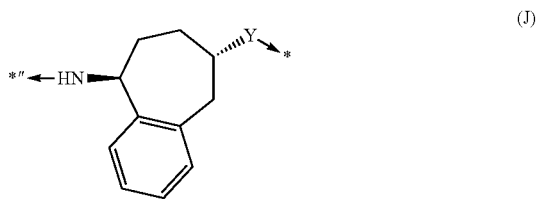

(J)

In formulae (B)-(J), Y is prefereably —O—.

In particular, the radical —N(H)-A-Y— may have formula (B), (C), (D), (E), (I) or (J) wherein Y is —O—.

The Group $R^2$

The group $R^2$ is a group of formula (IIIa-e) as defined above. Conveniently $R^2$ is a group (IIIb) or (IIIc) wherein $R^7$ and $R^8$ are ethyl or methyl.

One subclass of compounds of the invention has formula (IIIA):

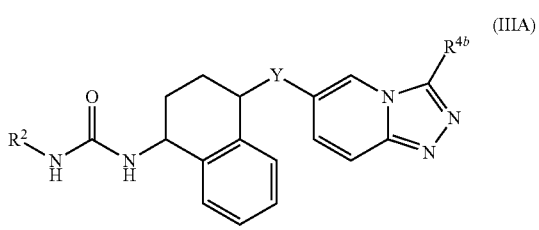

(IIIA)

wherein Y, $R^{4b}$ and $R^2$ as defined in relation to formula (I).

Another subclass of compounds of the invention has formula (IIIB):

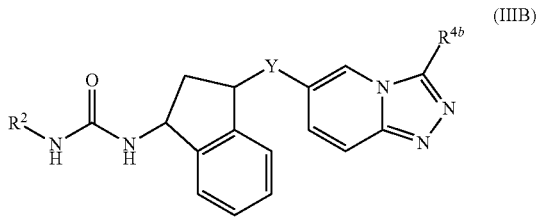

(IIIB)

wherein Y, $R^{4b}$ and $R^2$ as defined in relation to formula (I).

Another subclass of compounds of the invention has formula (IIIC):

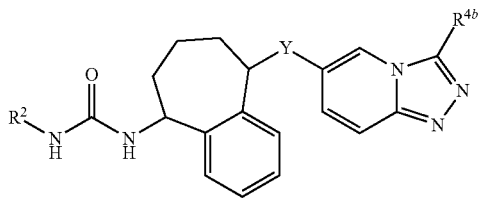

(IIIC)

wherein Y, R$^{4b}$ and R$^2$ as defined in relation to formula (I).

Another subclass of compounds of the invention has formula (IIID):

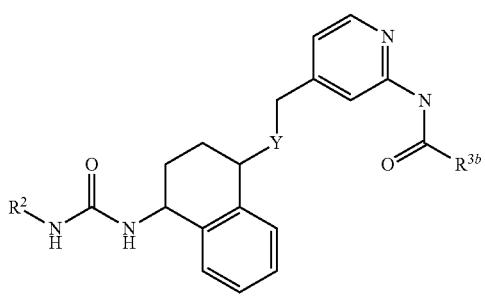

(IIID)

wherein Y, R$^{3b}$ and R$^2$ as defined in relation to formula (I).

Another subclass of compounds of the invention has formula (IIIE):

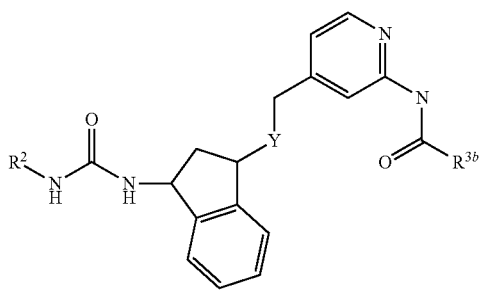

(IIIE)

wherein Y, R$^{3b}$ and R$^2$ as defined in relation to formula (I).

Another subclass of compounds of the invention has formula (IIIF):

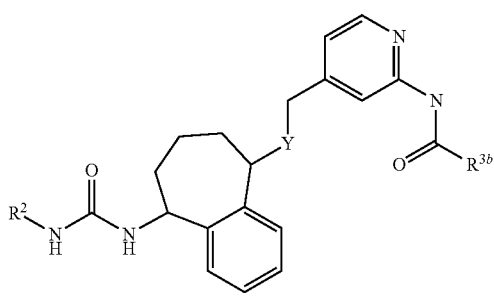

(IIIF)

wherein Y, R$^{3b}$ and R$^2$ as defined in relation to formula (I).

Utility

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

Compositions

As mentioned above, the compounds with which the invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases. For the purpose of the invention, inhaled administration is preferred.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane)

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

in the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321). Additionally, compounds of the invention may be delivered in multi-chamber devices thus allowing for delivery of combination agents.

Combinations

Other compounds may be combined with compounds with which the invention is concerned for the prevention and treatment of inflammatory diseases, in particular respiratory diseases. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028; (5) dual pharmacology M3-anticholinergic/132-adrenoreceptor agonists such as GSK961081; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412; (20) A2b antagonists such as those described in WO2002/42298; (21) modulators of chemokine receptor function, for example antagonists of CCR3 and CCR8; (22) compounds which modulate the action of other prostanoid receptors, for example a thromboxane A$_2$ antagonist; DP1 antagonists such as MK-0524, CRTH2 antagonists such as ODC9101 and AZD1981 and mixed DP1/CRTH2 antagonists such as AMG 009; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176; (26) CXCR2 or IL-8 antagonists such as SCH 527123 or GSK 656933; (27) IL-R signalling modulators such as kineret and ACZ 885; (28) MCP-1 antagonists such as ABN-912.

Methods of Synthesis

Compounds of the invention may be prepared by routine adaptation of the methods described in the Examples herein.

For example, of the invention may be prepared according to the routes illustrated in Scheme 1.

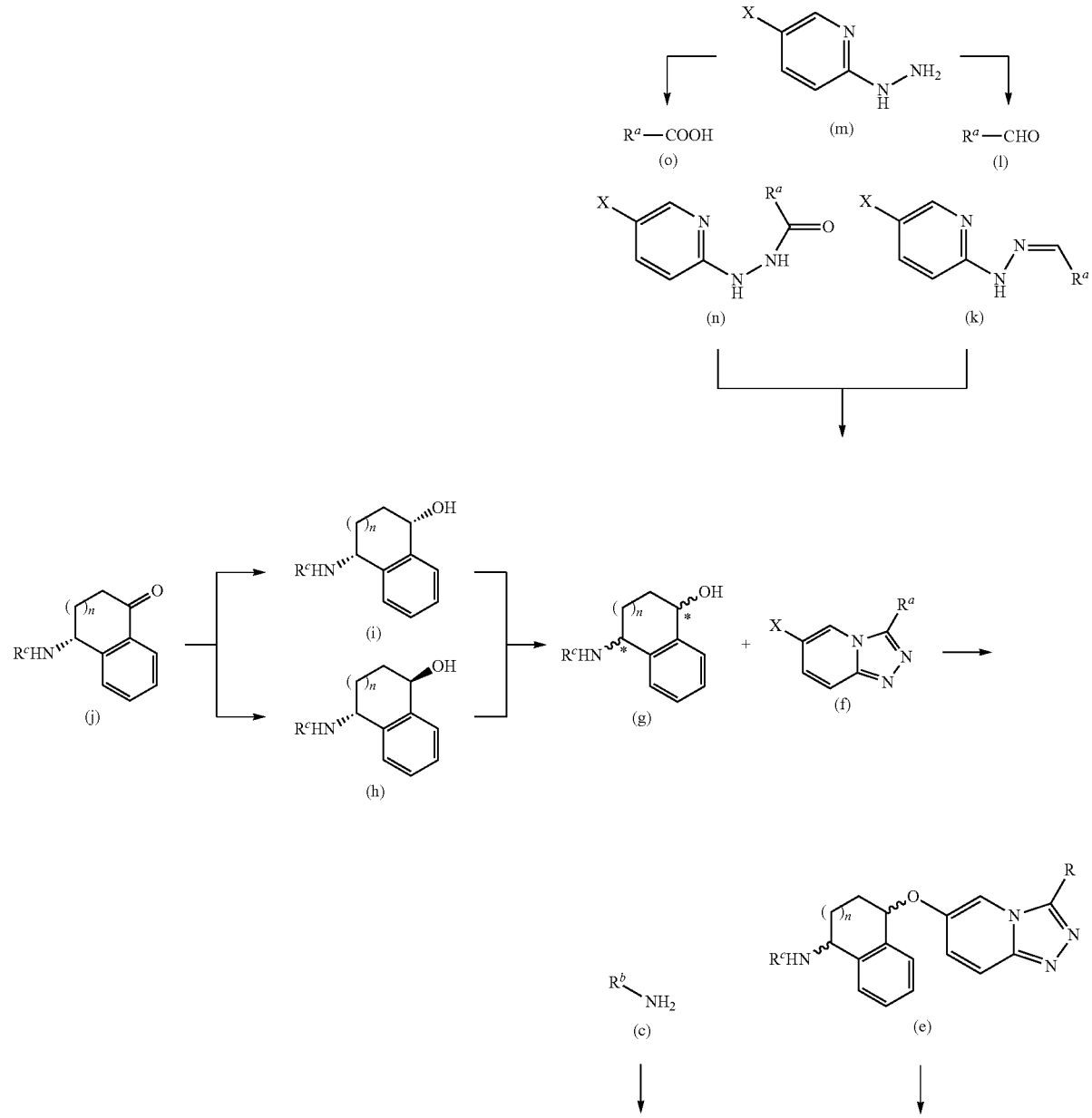

Scheme 1

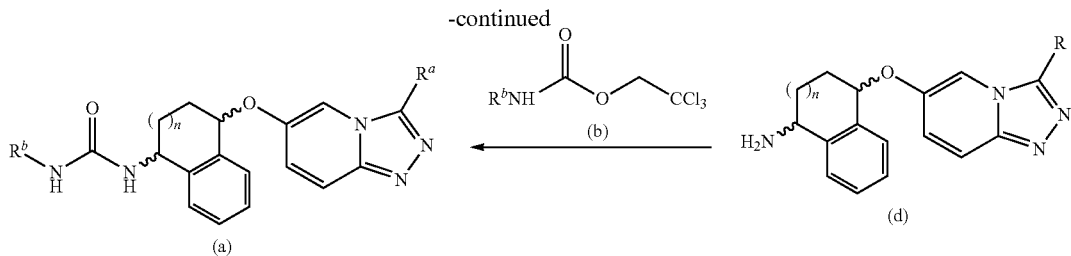

Compounds of general formula (a) may be prepared from compounds of general formula (d):

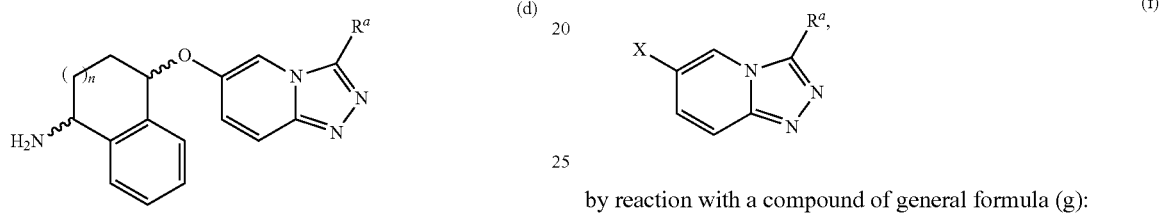

by reaction with a compound of general formula (b):

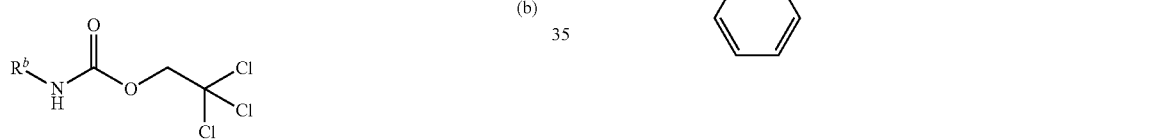

wherein R$^b$ is as defined for R$^2$ in general formula (I), in a suitable solvent such as dimethyl sulfoxide, 1,4-dioxane or acetonitrile, in the presence of a base such as diisopropylethylamine at a range of temperatures, preferably between room temperature and 100° C.

Compounds of general formula (b) may be prepared from amines of general formula (c) according to known literature procedures (e.g. WO2006009741, EP1609789).

Compounds of general formula (e), wherein R$^c$ is hydrogen may be prepared from compounds of general formula (e):

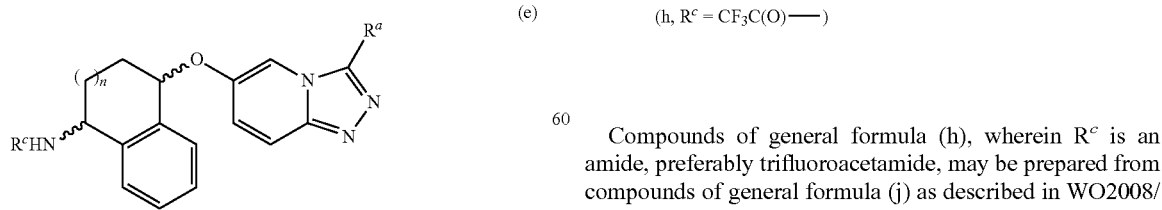

wherein R$^c$ may be a suitable protecting group by deprotection according to methods known to those skilled in the art.

Compounds of general formula (e) may be prepared from compounds of general formula (f):

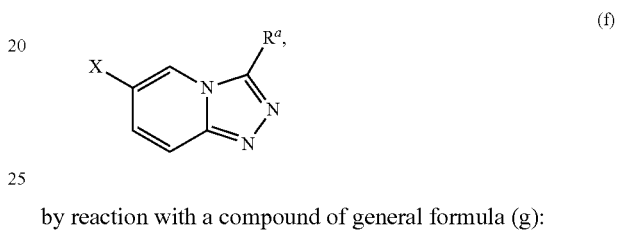

by reaction with a compound of general formula (g):

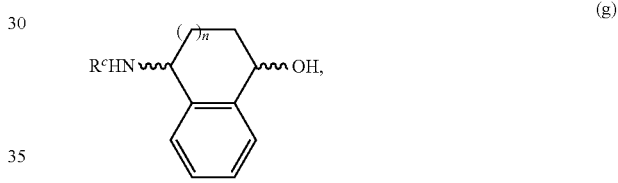

Using potassium tert-butoxide and 1,3-dimethyl-3,4,5,6-tetrahydro-2(1H)-pyrimidinone in in a suitable solvent such as toluene, 1,4-dioxane or acetonitrile at a range of temperatures, preferably between room temperature and 100° C.

Compounds of general formula (g), wherein R$^c$ is hydrogen may be prepared from compounds of general formula (h) or (i) as described in WO2008/043019.

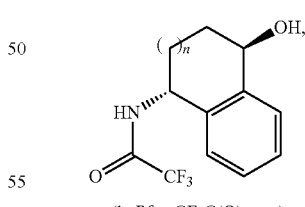

(h, R$^c$ = CF$_3$C(O)—)

Compounds of general formula (h), wherein R$^c$ is an amide, preferably trifluoroacetamide, may be prepared from compounds of general formula (j) as described in WO2008/043019 using RuCl[S,S-Tsdpen(p-cymene)]. It will be recognised that compounds of formula (j) may be homochiral as illustrated for (j) above, or be the opposite enantiomer or racemic.

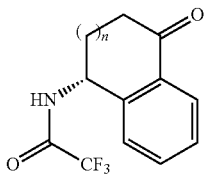
(j)

It will be realised by those skilled in the art that any combination of stereocentres as shown in (g) can be prepared using N—((R)-4-oxo-1,2,3,4-tetrahydro-naphthalen-1-yl)-acetamide or N—((S)-4-oxo-1,2,3,4-tetrahydro-naphthalen-1-yl)-acetamide using RuCl[R,R-Tsdpen(p-cymene)] or RuCl[S,S-Tsdpen(p-cymene)]. Compound (g) is drawn with no defined stereocentres but any combination can be reacted as illustrated in Scheme 1.

Compounds of general formula (f) may be prepared from compounds of general formula (k):

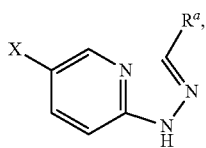
(k)

using a suitable oxidant such as chloramine T, lead tetracetate or phenyliodine(III) diacetate, in a suitable solvent such as dichloromethane or ethanol at a range of temperatures, preferably between room temperature and 100° C.

Compounds of general formula (k) may be prepared from compounds of general formula (m):

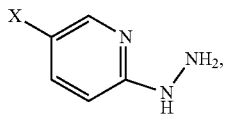
(m)

by reaction with an aldehyde of general formula (I):

 (I),

R$^a$CHO in a suitable solvent such as ethanol or tetrahydrofuran at a range of temperatures, preferably between room temperature and 80° C.

Alternatively, compounds of formula (f) may be prepared from compounds of formula (n):

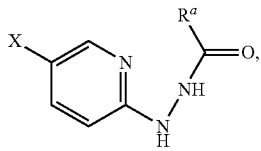
(n)

using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene or NMP, at a range of temperatures, preferably between room temperature and 120° C.

Compounds of formula (n) may be prepared from compounds of formula (m): reaction with a compound of general formula (o):

R$^a$CO$_2$H (o), using a suitable acylating/dehydrating agent such as triphenylphosphine/trichloroacetonitrile in the presence of a base such as diisopropylethylamine, in a suitable solvent such as dichloromethane or acetonitrile, at a range of temperatures, preferably between room temperature and 150° C.

General Experimental Details

Abbreviations used in the experimental section: aq.=aqueous; DCM=dichloromethane; DIPEA=diisopropylethylamine; DMF=N,N-dimethylformamide; DMSO=dimethyl sulfoxide; EDC=1-ethyl-3-(3'-dimethylaminopropyl)carbodiimide; EtOAc=ethyl acetate; EtOH=ethanol; Et$_2$O=diethyl ether; FCC=flash column chromatography; h=hour; HATU=2-(7-aza-1H-benzotriazole-1-yl)-1,1,3,3-tetramethyluronium hexafluorophosphate; HOBt=1-hydroxy-benzotriazole; HPLC=high performance liquid chromatography; LCMS=liquid chromatography mass spectrometry; MeCN=acetonitrile; MeOH=methanol; min=minutes; NMR=nuclear magnetic resonance; RT=room temperature; Rt=retention time; sat.=saturated; SCX-2=strong cation exchange chromatography; TFA=trifluoroacetic acid; THF=Tetrahydrofuran; H$_2$O=water; IMS=industrial methylated spirit; Et$_3$N=triethylamine; EtNiPr$_2$=diisopropylethylamine The nomenclature of structures was assigned using Autonom 2000 Name software from MDL Inc. Stereochemical assignments of compounds are based on comparisons with data reported in WO2008/043019 for key intermediates. All reactions were carried out under an atmosphere of nitrogen unless specified otherwise.

NMR spectra were obtained on a Varian Unity lnova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane. NMR spectra were assigned using DataChord Spectrum Analyst Version 4.0.b21.

Where products were purified by flash column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d Genesis column with 7 μm particle size), or a Phenyl-Hexyl column (250×21.2 mm i.d. Gemini column with 5 μm particle size), UV detection at 230 or 254 nm, flow 5-20 mL/min), eluting with gradients from 100-0 to 0-100% water/acetonitrile (containing 0.1% TFA or 0.1% formic acid) or water/MeOH (containing 0.1% TFA or 0.1% formic acid). Fractions containing the required product (identified by LCMS analysis) were pooled, the organic fraction removed by evaporation, and the remaining aqueous fraction lyophilised, to give the final product. Products purified by preparative HPLC were isolated as formate or TFA salts, unless otherwise stated.

The Liquid Chromatography Mass Spectroscopy (LCMS) and HPLC systems used are:

Method 1

Waters Platform LC Quadrupole mass spectrometer with a C18-reverse-phase column (30×4.6 mm Phenomenex Luna 3 μm particle size), elution with A: water+0.1% formic acid; B: methanol+0.1% formic acid Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (200 μL split to MS with in-line HP1100 DAD detector).
MS ionization method - Electrospray (positive and negative ion).

Method 2

Waters ZMD quadrupole mass spectrometer with a C18-reverse-phase column (30×4.6 mm Phenomenex Luna 3 μm particle size), elution with A: water +0.1% formic acid; B: methanol+0.1% formic acid Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (200 μL split to MS with in-line Waters 996 DAD detector).
MS ionization method - Electrospray (positive and negative ion).

Method 3

Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (200 μL split to MS with in-line HP1100 DAD detector).
MS ionization method - Electrospray (positive and negative ion).

Method 4

Waters ZMD quadrupole mass spectrometer with an Higgins Clipeus 5 micron C18 100×3.0 mm, maintained at 40° C. Elution with A: water+0.1% formic acid; B: MeOH+0.1% formic acid Gradient:

| Gradient - Time | flow mL/min | % A | % B |
| --- | --- | --- | --- |
| 0.00 | 1.0 | 85 | 15 |
| 1.00 | 1.0 | 85 | 15 |
| 13.00 | 1.0 | 5 | 85 |
| 20.00 | 1.0 | 5 | 85 |
| 22.00 | 1.0 | 85 | 15 |

Detection - MS, UV PDA.
MS ionization method - Electrospray (positive and negative ion).

Method 5

Waters ZMD quadrupole mass spectrometer with an Acquity BEH C18 1.7 um 100×2.1 mm, Acquity BEH Shield RP18 1.7 um 100×2.1 mm or Acquity HSST3 1.8 um 100×2.1 mm, maintained at 40° C. Elution with A: water+0.1% formic acid; B: CH$_3$CN+0.1% formic acid Gradient:

| Gradient - Time | flow mL/min | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection - MS, UV PDA.
MS ionization method - Electrospray (positive and negative ion).

Method 6

Phenomenex Gemini C18-reverse-phase column (250×21.20 mm 5 μm particle size), elution with A: water+ 0.1% formic acid; B: CH$_3$CN+0.1% formic acid Gradient— 10% A/90% B to 98% λ/2% B over 20 min—flow rate 18 mL/min. Detection—In-line UV detector set at 254 nM wavelength.

EXAMPLE 1

(+/−) 1-(5-tert-Butyl-2-p-tolyl-2H-pyrazol-3-yl)-3-[4-(3-isopropyl-[1,2,4]-triazolo[4,3-a]pyridin-6-yloxy)-cis-1,2,3,4-tetrahydro-naphthalen-1-yl]-urea a. (+/−) Cis 4-azido-1,2,3,4-tetrahydro-naphthalen-1-ol A solution of 1-tetralone (2.92 g, 20 mmol), N-bromosuccinimide (3.56 g, 20 mmol) and azodibutyronitrile (80 mg) in carbon tetrachloride (80 mL) was refluxed for 1.25h, then evaporated in vacuo. The resulting oil was dissolved in DMF (8 mL), treated with sodium azide (2.6 g, 40 mmol) and stirred at RT for 2h. The reaction mixture was partitioned between Et$_2$O (200 mL) and H$_2$O (50 mL). The resulting organic layer was dried (MgSO$_4$), filtered and evaporated in vacuo. The resulting oil was dissolved in EtOH (100 mL), cooled to 0° C. under argon and treated with sodium borohydride (0.76 g, 20 mmol). The reaction mixture was stirred at RT for 1h, concentrated in vacuo to approx. 50 mL and partitioned between $H_2O$ and $Et_2O$. The aqueous layer was extracted with DCM (100 mL) and EtOAc (100 mL) and the combined organic layers were dried ($MgSO_4$), filtered, concentrated in vacuo and purified by FCC using 0-30% cyclohexane/diethyl ether to give the title compound at Rf 0.2 as a dark red oil (1.5 g, 40%). $^1$H NMR (300 MHz, $CDCl_3$): 7.57-7.52 (1 H, m), 7.43-7.28 (3 H, m), 4.81-4.72 (1 H, m), 4.55-4.49 (1 H, m), 2.13-1.99 (3 H, m), 1.79 (1 H, m).

b. (+/−) Cis 4-amino-1,2,3,4-tetrahydro-naphthalen-1-ol

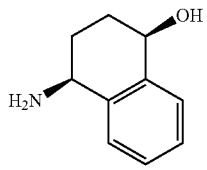

A solution of example 1 step a (1.086 g, 5.7 mmol) and triphenylphosphine (1.81 g, 6.84 mmol) in THF (20 mL) and $H_2O$ (4 mL) was stirred at RT under a nitrogen atmosphere for 6.5h. The reaction mixture was diluted with $Et_2O$ and extracted with 0.4M HCl solution. The aqueous layer was basified with 10N sodium hydroxide solution and extracted with DCM. The combined organic layers were dried ($MgSO_4$), filtered, concentrated in vacuo and purified by FCC using 0-20% DCM/2M $NH_3$ in MeOH to give the title compound (0.55 g, 59%). LCMS (method 1): Rt 0.41, 1.50 min, m/z 164 [MH$^+$].

c. Isobutyric acid N'-(5-fluoro-pyridin-2-yl)-hydrazide

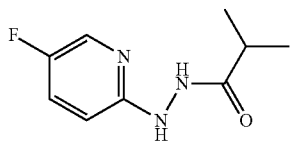

A solution of 5-fluoro-2-hydrazinyl-pyridine (0.59 g, 4.65 mmol), isobutyric acid (528 mg, 6 mmol), and HOBt hydrate (153 mg, 1 mmol) in DCM (10 mL) was treated with EDC (1.15 g, 6 mmol). The reaction mixture was stirred at RT for 40 min, poured onto sat. aq. sodium bicarbonate (40 mL), extracted with four portions of DCM, dried ($Na_2SO_4$), evaporated and purified by FCC using 10-30% EtOAc/DCM to give the title compound (0.42 g, 46%). LCMS (method 2): Rt 2.46 min, m/z 198 [MH$^+$].

d. 6-Fluoro-3-isopropyl-[1,2,4]triazolo[4,3-a]pyridine

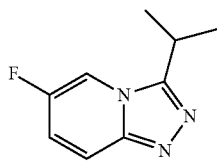

A solution of Example 1 step c (0.41 g, 2.08 mmol), triphenylphosphine (763 mg, 2.91 mmol) and triethylamine (0.87 mL, 6.24 mmol) in THF (5 mL) at 0° C. was treated with 1,2-hexachloroethane (690 mg, 2.91 mmol). The reaction mixture was stirred at 0° C. for 40 min then at RT for 20 min, quenched with water, extracted twice with EtOAc, dried ($Na_2SO_4$), evaporated and purified twice by FCC (cyclohexane/EtOAc 1/0 to 1/1) to afford the title compound (274 mg, contaminated with 20% $PPh_3O$, 58%) as a white solid. LCMS (method 1): Rt 2.58 min, m/z 180 [MH$^+$].

e. (+/−) 4-(3-Isopropyl-[1,2,4]-triazolo[4,3-a]pyridin-6-yloxy)-cis-1,2,3,4-tetrahydro-naphthalen-1-ylamine

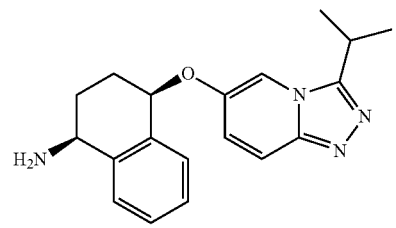 [SMILES: CC(C)c1nnc2ccc(O[C@@H]3CC[C@H](N)c4ccccc43)cn12]

A solution of Example 1 step b (367 mg, 2.05 mmol) and potassium tert-butoxide (255 mg, 2.25 mmol) in toluene (1 mL) and 1,3-dimethyl-3,4,5,6-tetrahydro-2(1H)-pyrimidinone (0.5 mL) was added example 1, step d (334 mg, 2.05 mol). The reaction mixture was stirred while the temperature was increased from 50° C. to 80° C. over 20 min. The reaction was cooled, quenched with water and extracted with 10% citric acid. The aqueous phase was washed with $CH_2Cl_2$, basified with KOH to pH10 and extracted with $CH_2Cl_2$. The combined organic layers were dried ($MgSO_4$), concentrated and purified by FCC (0-9% MeOH/$NH_3$—$CH_2Cl_2$) to give the title compound as a brown gum which solidified on standing (400 mg, 60%). LCMS (method 3): Rt 2.45 min, m/z 323 [MH$^+$]. $^1$H NMR (400 MHz, $CDCl_3$): 1.43-1.55 (6H, m), 1.85-2.15 (3H, m), 2.30-2.45 (1H, m), 3.27 (1H, q, J 6.85), 3.97-4.04 (1H, m), 5.24 (1H, t, J 4.7), 5.29 (1H, s), 7.07-7.14 (1H, m), 7.22-7.50 (5H, m), 7.56-7.62 (1H, m), 7.65-7.71 (1H, m).

f. (+/−) 1-(5-tert-Butyl-2-p-tolyl-2H-pyrazol-3-yl)-3-[4-(3-isopropyl-[1,2,4]triazolo[4,3-a]pyridin-6-yloxy)-cis-1,2,3,4-tetrahydro-naphthalen-1-yl]-urea A solution of Example 1e (87 mg, 0.27 mmol) in dioxane (2 mL) with EtNiPr$_2$ (49 uL, 0.3 mmol) and 2,2,2-trichloroethyl 3-tert-butyl-1-p-tolyl-1H-pyrazol-5-ylcarbamate (109 mg, 0.27 mmol) was heated at 70° C. for 20h. The reaction was allowed to cool, partitioned between $H_2O$-EtOAc, the organic phase dried ($Na_2SO_4$) and concentrated in vacuo. The residue was purified by FCC (0-6% 9:1 MeOH/0.88 $NH_3$—$CH_2Cl_2$) and slurried in MeOH to give the title compound as a colourless solid (57 mg). LCMS (method 4): Rt 12.03 min, m/z 578 [MH$^+$]. $^1$H NMR (400 MHz, $CDCl_3$): 7.59 (1 H, d, J 9.8), 7.42 (1 H, d, J 1.9), 7.39 (2 H, d, J 8.2), 7.32-7.24 (4 H, m), 7.20 (2 H, d, J 8.1), 7.03 (1 H, dd, J 9.8, 1.9), 6.52 (1 H, bs), 6.28 (1 H, s), 5.47 (1 H, d, J 8.7), 5.19 (1 H, t, J 3.9), 5.09 (1 H, td, J 8.9, 5.2), 3.29-3.18 (1 H, m), 2.35 (3 H, s), 2.25 (1 H, m), 2.13-2.03 (2 H, m), 1.93 (1H, m), 1.47 (3 H, d, J 6.9), 1.44 (3 H, d, J 6.9), 1.32 (9 H, s).

EXAMPLE 2

(+/−) 1-(5-tert-Butyl-2-p-tolyl-2H-pyrazol-3-yl)-3-[4-(3-isopropyl[1,2,4]triazolo[4,3-a]pyridin-6-yloxy)-trans-1,2,3,4-tetrahydro-naphthalen-1-yl]-urea

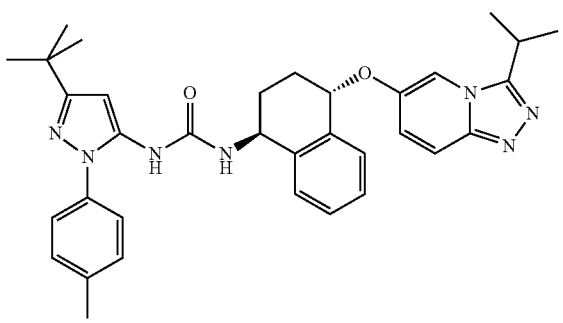 [SMILES: Cc1ccc(-n2nc(C(C)(C)C)cc2NC(=O)N[C@H]2CC[C@H](Oc3ccc4nnc(C(C)C)n4c3)c3ccccc32)cc1]

a. (+/−) Trans 4-azido-1,2,3,4-tetrahydro-naphthalen-1-ol

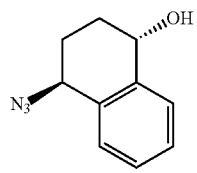 [SMILES: [N-]=[N+]=N[C@H]1CC[C@H](O)c2ccccc21]

The title compound was obtained from Example 1 step a by FCC (cyclohexane/diethyl ether 100/0 to 70/30) at Rf 0.1 as a dark red oil (0.4 g). ¹H NMR (300 MHz, CDCl₃): 7.57-7.52 (1 H, m), 7.43-7.28 (3 H, m), 4.81-4.72 (1 H, m), 4.55-4.49 (1 H, m), 2.13-1.99 (3 H, m), 1.79 (1 H, m).

b. (+/−) Trans 4-amino-1,2,3,4-tetrahydro-naphthalen-1-ol

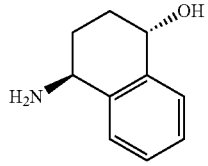

A solution of example 2 step b (0.3 g, 1.59 mmol) and triphenylphosphine (0.5 g, 1.9 mmol) in THF (10 mL) and H₂O (4 mL) was stirred at RT under a nitrogen atmosphere for 6.5h. The reaction mixture was diluted with Et₂O and extracted with 0.5 M HCl solution. The aqueous layer was basified with K₂CO₃ solution and extracted with DCM. The combined organic layers were dried (MgSO₄), filtered, concentrated in vacuo and purified by FCC (DCM/MeOH containing NH₃ 9/1) to give the title compound (113 mg). LCMS (method 1): Rt 0.41, 1.50 min, m/z 164 [MH⁺].

b. (+/−) 1-(5-tert-Butyl-2-p-tolyl-2H-pyrazol-3-yl)-3-[4-(3-isopropyl-[1,2,4]triazolo[4,3a]pyridin-6-yloxy)-trans-1,2,3,4-tetrahydro-naphthalen-1-yl]-urea

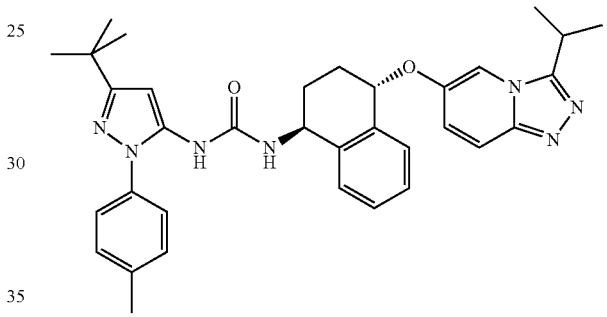

The title compound was prepared in a similar manner to Example 1 steps e and f starting from the product of Example 2 step b. LCMS (method 4): Rt 12.01 min, m/z 578 [MH⁺]. ¹H NMR (400 MHz, CDCl₃): 7.59 (1 H, d, J 9.2), 7.43 (1 H, d, J 1.5), 7.35 (2 H, d, J 8.1), 7.32-7.25 (4 H, m), 7.19 (2 H, d, J 8.4), 7.09 (1 H, dd, J 9.8, 1.8), 6.49 (1 H, bs), 6.25 (1 H, s), 5.38 (1 H, d, J 8.3), 5.23 (1 H, t, J 5.0), 5.16 (1 H, q, J 6.3), 3.23 (1 H, m), 2.40-2.30 (4 H, m), 2.19-2.06 (2 H, m), 1.85-1.75 (1 H, m), 1.46 (3 H, d, J 6.9), 1.43 (3 H, d, J 6.9), 1.31 (9 H, s).

The following examples were prepared in a similar manner to Example 1.

| Example No. | Structure | NMR (400 MHz) δ | LCMS |
|---|---|---|---|
| 3 | ![structure] | (CDCl₃): 1.31 (9H, s), 1.80-1.93 (1H, m), 1.94-2.09 (2H, m), 2.17-2.28 (1H, m), 2.36 (3H, s), 4.99-5.09 (1H, m), 5.10-5.18 (2H, m), 6.18 (1H, s), 6.24 (1H, s), 7.11 (1H, dd, J 2.0, 8.0), 7.17-7.31 (6H, m), 7.34-7.40 (3H, m), 7.44-7.61 (3H, m), 7.67 (1H, dd, 1.6, 7.6), 7.72-7.76 (1H, m). | (Method 5): Rt 5.22 min, m/z 646[MH⁺]. |

| Example No. | Structure | NMR (400 MHz) δ | LCMS |
|---|---|---|---|
| | (+/−)1-(5-tert-Butyl-2-p-tolyl-2H-pyrazol-3-yl)-3-{4-[3-(2-chloro-phenyl)-[1,2,4]triazolo[4,3-a]pyridin-6-yloxy]-cis-1,2,3,4-tetrahydro-naphthalen-1-yl}-urea | | |
| 4 | 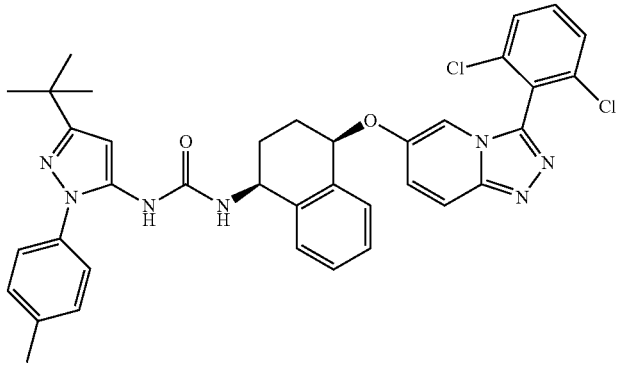 [SMILES: Cc1ccc(-n2nc(C(C)(C)C)cc2NC(=O)N[C@H]2CC[C@@H](Oc3ccc4nnc(-c5c(Cl)cccc5Cl)n4c3)c3ccccc32)cc1] | (d<sub>6</sub>-DMSO) 1.26 (9H, s), 1.75-2.10 (4H, m), 2.35 (3H, s), 4.73-4.81 (1H, m), 5.48-5.53 (1H, m), 6.31 (1H, m), 7.05 (1H, d, J 8.0), 719-7.38 (9H, m), 7.67-7.78 (3H, m), 7.89 (1H, d, J 12.0), 7.96 (1H, s), 8.03 (1H, s) | (Method 5): Rt 5.30 min, m/z 680 [MH<sup>+</sup>]. |
| | (+/−)1-(5-tert-Butyl-2-p-tolyl-2H-pyrazol-3-yl)-3-{4-[3-(2,6-dichloro-phenyl)[1,2,4]triazolo[4,3-a]pyridin-6-yloxy]-cis-1,2,3,4-tetrahydro-naphthalen-1-yl}-urea | | |
| 5 | 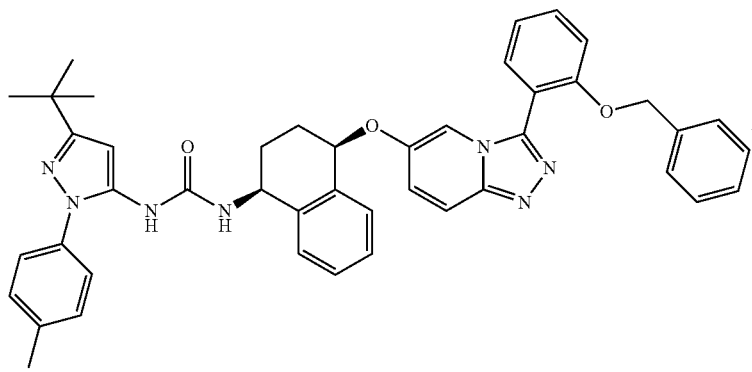 [SMILES: Cc1ccc(-n2nc(C(C)(C)C)cc2NC(=O)N[C@H]2CC[C@@H](Oc3ccc4nnc(-c5ccccc5OCc5ccccc5)n4c3)c3ccccc32)cc1] | (d<sub>4</sub>-MeOH) 1.32 (9H, s), 1.66-1.98 (4H, m), 2.40 (3H, s), 4.73-4.84 (1H, m), 5.13 (1H, t, J 4.7), 5.19 (2H, s), 6.35 (1H, s), 7.04-7.40 (18H, m), 7.60-7.68 (3H, m), 7.73 (1H, d, J 9.5) | (Method 4): Rt 12.5 min, m/z 717 [MH<sup>+</sup>]. |
| | (+/−) 1-{4-[3-(2-Benzyloxy-phenyl)-[1,2,4]triazolo[4,3-a]pyridin-6-yloxyl-cis-1,2,3,4-tetrahydro-naphthalen-1-yl}-3-(5-tert-butyl-2-p-tolyl-2H-pyrazol-3-yl)-urea | | |
| 6 | 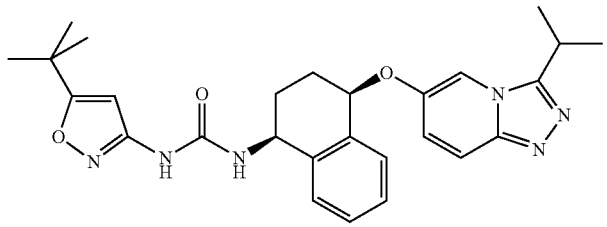 [SMILES: CC(C)c1nnc2ccc(O[C@@H]3CC[C@H](NC(=O)Nc4cc(C(C)(C)C)on4)c4ccccc43)cn12] | (d<sub>6</sub>-DMSO): 1.28 (9H, s), 1.38 (6H, t, J 7.2), 1.85-2.22 (4H, m), 3.57 (q, 1H, J 6.6), 4.87-4.95 (1H, m), 5.55 (1H, t, J 4.17), 6.40 (1H, s), 7.02 (1H, d, J 9.0), 7.22 (1H, dd, J 10, 2.4), 7.27-7.45 (4H, m), 7.69 (1H, d, J 10.0), 8.21-8.24 (1H, m), 9.32 (1H, s). | (Method 5): Rt 4.35 min, m/z 488 [MH<sup>+</sup>]. |
| | (+/−) 1-(5-tert-Butyl-isoxazol-3-yl)-3-[4-(3-isopropyl-[1,2,4]triazolo[4,3-a]pyridin-6-yloxy)-cis-1,2,3,4-tetrahydro-naphthalen-1-yl]-urea | | |

EXAMPLE 7

(+/−) 1-(5-tert-Butyl-2-p-tolyl-2H-pyrazol-3-yl)-3-{4-[3-(2-hydroxy-phenyl) [1,2,4]triazolo[4,3-a]pyridin-6-yloxy]-cis-1,2,3,4-tetrahydro-naphthalen-1-yl}-urea

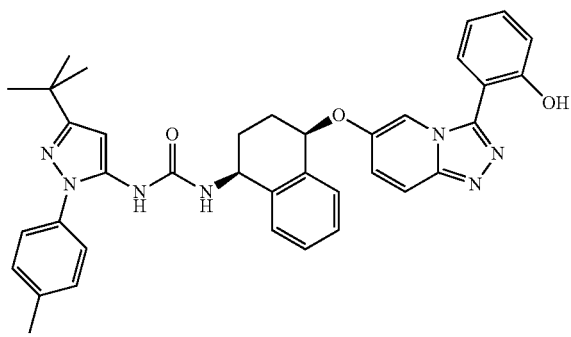 [SMILES: Cc1ccc(-n2nc(C(C)(C)C)cc2NC(=O)N[C@H]2CC[C@@H](Oc3ccc4nnc(-c5ccccc5O)n4c3)c3ccccc32)cc1]

A solution of Example 5 (50 mg, 69.6 mmol) in IMS (5 mL) was stirred with palladium hydroxide (20 mg) under an atmosphere of hydrogen for 24 h. The reaction was filtered through Hyflo, concentrated in vacuo and purified using prep HPLC method 6. Product containing fractions were freeze dried to give the title compound as an off white solid. LCMS (Method 5): Rt 4.87 min, m/z 627 [MH$^+$]. $^1$H NMR (400 MHz, d$_4$-MeOH): 1.31 (9H, s), 1.86-2.33 (4H, m), 2.39 (3H, s), 4.85-4.91 (1H, m), 5.33 (1H, t, J 4.1), 6.34 (1H, s), 7.02-7.08 (2H, m), 7.19-7.36 (12H, m), 7.42-7.48 (1H, m), 7.58 (1H, dd, J 2.7, 8.3), 7.69-7.75 (2H, m).

EXAMPLE 8

1-(5-tert-Butyl-2-p-tolyl-2H-pyrazol-3-yl)-3-[(1R,4R)-4-(3-isopropyl-[1,2,4]triazolo[4,3-a]pyridin-6-yloxy)-1,2,3,4-tetrahydro-naphthalen-1-yl]-urea

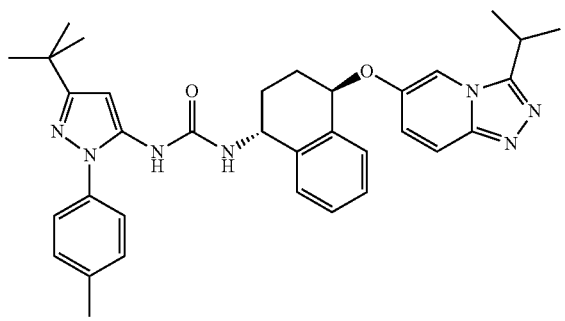 [SMILES: Cc1ccc(-n2nc(C(C)(C)C)cc2NC(=O)N[C@@H]2CC[C@@H](Oc3ccc4nnc(C(C)C)n4c3)c3ccccc32)cc1]

The title compound was prepared using (1R,4R)-4-amino-1,2,3,4-tetrahydro-naphthalen-1-ol (WO2008/043019) in a similar manner to Example 1, steps e and f. LCMS (Method 5): Rt 4.71 min, m/z 578 [MH$^+$]. $^1$H NMR (400 MHz, d$_6$-DMSO): 1.26 (9H, s), 1.35-1.41 (6H, m), 1.69-1.80 (1H, m), 1.97-2.07 (1H, m), 2.08-2.19 (2H, m), 2.35 (3H, s), 3.56 (1H, q, J 6.95), 4.86-4.93 (1H, m), 5.53-5.59 (1H, m), 6.32 (1H, s), 7.01 (1H, d, J 8.34), 7.20-7.43 (9H, m), 7.68 (1H, d, J 10.4), 7.96 (1H, s), 8.19-8.22 (1H, m).

EXAMPLE 9

1-(5-tert-Butyl-2-p-tolyl-2H-pyrazol-3-yl)-3-[(1R,4S)-4-(3-isopropyl-[1,2,4]triazolo[4,3-a]pyridin-6-yloxy)-1,2,3,4-tetrahydro-naphthalen-1-yl]-urea

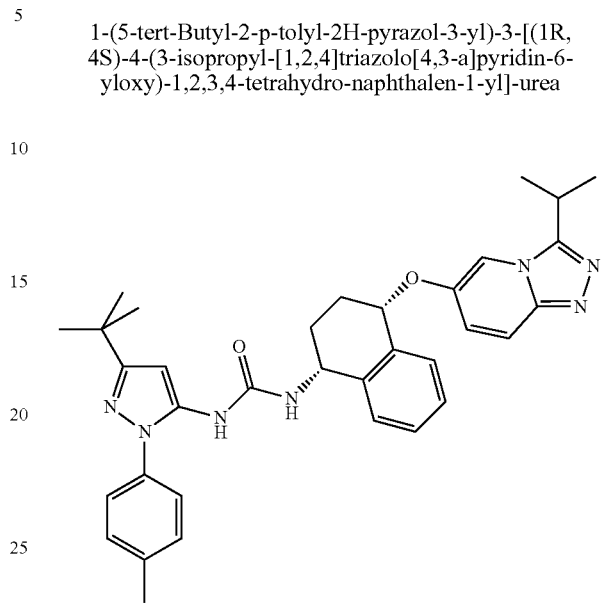

a. 2,2,2-Trifluoro-N-((1R,4S)-4-hydroxy-1,2,3,4-tetrahydro-naphthalen-1-yl)-acetamide

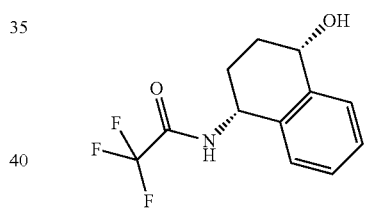

The title compound was prepared as described for 2,2,2-trifluoro-N-((1R,4R)-4-hydroxy-1,2,3,4-tetrahydronaphthalene-1-yl)acetamide in WO2008/043019 using RuCl[(S,S)-Tsdpen(cymene)]. $^1$H NMR (400 MHz, d$_6$-DMSO): 1.61-1.82 (2H, m), 2.04-2.16 (2H, m), 4.56-4.64 (1H, m), 5.03-5.13 (1H, m), 5.28 (1H, d, J 7.5), 7.06 (1H, d, J 7.5), 7.21-7.32 (2H, m), 7.49 (1H, d, J 7.5), 9.79 (1H, d, J 8.5).

b. (1S,4R)-4-Amino-1,2,3,4-tetrahydro-naphthalen-1-ol

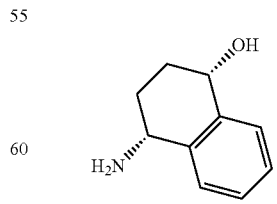

The title compound was prepared using Example 9, step a as described in WO2008/043019. $^1$H NMR (400 MHz, d$_6$-DMSO): 1.80-1.93 (4H, m), 3.98-4.02 (1H, m), 4.50-4.55 (1H, m), 7.21-7.28 (2H, m), 7.39-7.47 (2H, m).

c. 1-(5-tert-Butyl-2-p-tolyl-2H-pyrazol-3-yl)-3-[(1R,4S)-4-(3-isopropyl-[1,2,4]triazolo[4,3-a]pyridin-6-yloxy)-1,2,3,4-tetrahydro-naphthalen-1-yl]-urea The title compound was prepared using (1S,4R)-4-amino-1,2,3,4-tetrahydro-naphthalen-1-ol (Example 9, step b) in a similar manner to Example 1, steps e and f. LCMS (Method 5): Rt 4.84 min, m/z 578 [MH$^+$]. $^1$H NMR (400 MHz, d$_6$-DMSO): 1.27 (9H, s), 1.35-1.40 (6H, m), 1.80-1.98 (2H, m), 2.02-2.13 (2H, m), 2.36 (3H, s), 3.56 (1H, q, J 7.2), 4.78-4.86 (1H, m), 5.53 (1H, t, J 5.2), 5.75 (1H, s), 6.32 (1H, s), 7.09 (1H, d, J 8.3), 7.16 (1H, dd, J 9.7, 2.0), 7.25-7.41 (7H, 7.68 (1H, d, J 9.7), 8.03 (1H, s), 8.19-8.22 (1H, m).

EXAMPLE 10

1-(5-tert-Butyl-2-p-tolyl-2H-pyrazol-3-yl)-3-[(1S,4R)-4-(3-isopropyl-[1,2,4]triazolo[4,3-a]pyridin-6-yloxy)-1,2,3,4-tetrahydro-naphthalen-1-yl]-urea

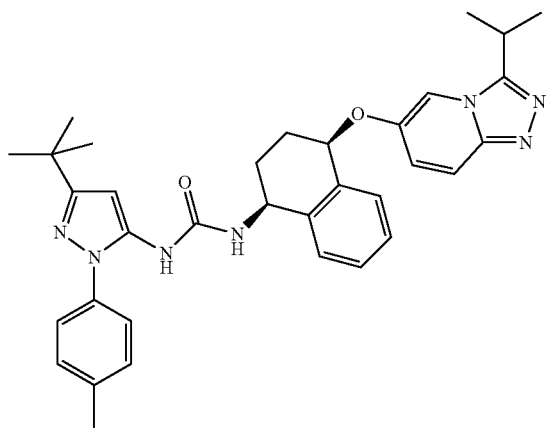 [SMILES: Cc1ccc(-n2nc(C(C)(C)C)cc2NC(=O)N[C@H]2CC[C@@H](Oc3ccc4nnc(C(C)C)n4c3)c3ccccc32)cc1]

The title compound was prepared using (1R,4S)-4-amino-1,2,3,4-tetrahydro-naphthalen-1-ol in a similar manner to Example 1, steps e and f. LCMS (Method 5): Rt 4.85 min, m/z 578 [MH$^+$]. $^1$H NMR (400 MHz, CDCl$_3$): 1.32 (9H, s), 1.42-1.49 (6H, m), 1.86-1.98 (1H, m), 2.01-2.13 (2H, m), 2.21-2.30 (1H, m), 3.35 (3H, s), 3.24 (1H, q, J 6.8), 5.04-5.13 (1H, m), 5.17-5.21 (1H, m), 5.45 (1H, d, J 8.6), 6.27 (1H, s), 6.53 (1H, s), 7.04 (1H, dd, J 9.7, 2.1), 7.20 (1H, d, J 8.0), 7.23-7.44 (8H, m), 7.59 (1H, d, J 9.9).

EXAMPLE 11

1-(5-tert-Butyl-2-p-tolyl-2H-pyrazol-3-yl)-3-[(1S,4S)-4-(3-isopropyl-[1,2,4]triazolo[4,3-a]pyridin-6-yloxy)-1,2,3,4-tetrahydro-naphthalen-1-yl]-urea

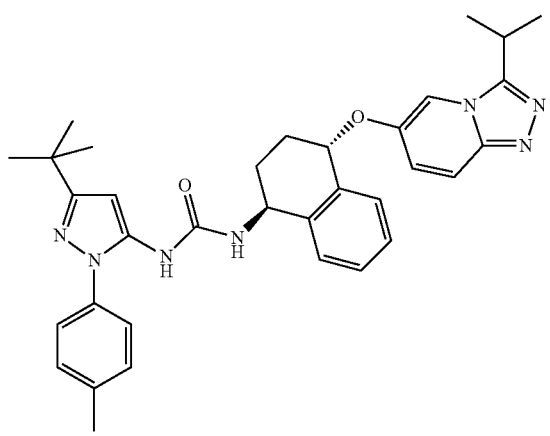 [SMILES: Cc1ccc(-n2nc(C(C)(C)C)cc2NC(=O)N[C@H]2CC[C@H](Oc3ccc4nnc(C(C)C)n4c3)c3ccccc32)cc1]

The title compound was prepared using (1S,4S)-4-amino-1,2,3,4-tetrahydro-naphthalen-1-ol and in a similar manner to Example 1, steps e and f. LCMS (Method 5): Rt 4.74 min, m/z 578 [MH$^+$]. $^1$H NMR (400 MHz, CDCl$_3$): 1.30 (9H, s), 1.40-1.48 (6H, m), 1.70-1.87 (4H, m), 2.07-2.19 (2H, m), 2.33 (3H, s), 3.23 (1H, q, J 5.2), 5.11-5.19 (1H, m), 5.20-5.27 (1H, m), 5.46 (1H, d, J 7.8), 6.25 (1H, s), 6.58 (1H, s), 7.10 (1H, d, J 9.5), 7.17 (1H, d, J 8.2), 7.23-7.37 (4H, m), 7.44 (1H, s), 7.58 (1H, d, J 9.5).

EXAMPLE 12

1-(5-tert-Butyl-2-p-tolyl-2H-pyrazol-3-yl)-3-[(1R,3R)-3-(3-isopropyl[1,2,4]triazolo[4,3a]pyridin-6-yloxy)-indan-1-yl]urea

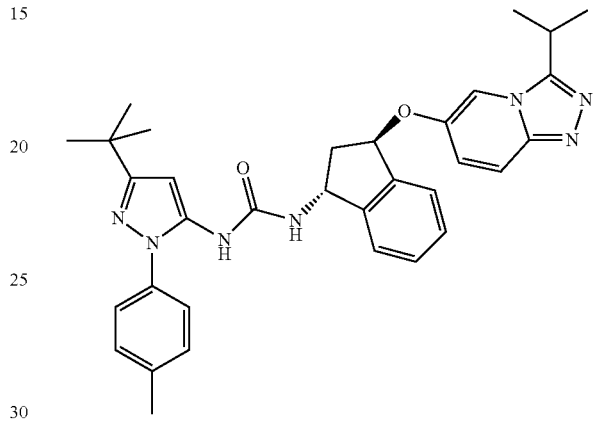

(R)-3-amino-indan-1-one (EP1316542A1) was prepared from (R)—(N-acetyl)-β-alanine as described in EP1316542A1. Bioorg. MedChem. Lett, 2008, 18, 4224-4227 and Chem. Lett., 2002, (3), 266. (1R,3R)-3-amino-indan-1-ol was prepared from (R)-3-amino-indan-1-one using proceedures described in WO2008/043019. The title compound was prepared using (1R,3R)-3-amino-indan-1-ol in a similar manner to Example 1, steps e and f. LCMS (Method 5): Rt 4.61 min, m/z 564 [MH$^+$]. $^1$H NMR (400 MHz, CDCl$_3$): 1.31 (9H, s), 1.42-1.48 (6H, m), 2.14-2.25 (1H, m), 2.34 (3H, s), 2.82 (1H, dd, J 3.2, 15.3), 3.23 (1H, q, J 6.4) 5.56-5.71 (3H, m), 6.27 (1H, s), 6.62 (1H, s), 7.05 (1H, d, J 9.7), 7.15-7.22 (2H, m), 7.23-7.45 (7H, m), 7.56 (1H, d, 10.5).

EXAMPLE 13

1-(5-tert-Butyl-2-p-tolyl-2H-pyrazol-3-yl)-3-[(1S,3S)-3-(3-isopropyl-[1,2,4]triazolo[4,3-a]pyridin-6-yloxy)-indan-1-yl]-urea

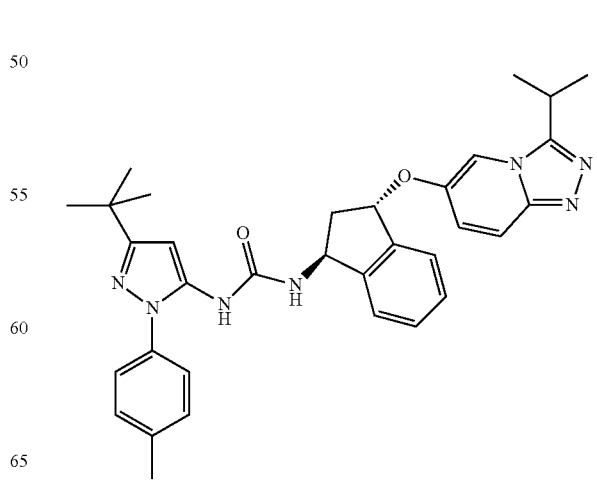

The title compound was prepared using (1S,3S)-3-amino-indan-1-ol in a similar manner to Example 12. LCMS (Method 5): Rt 4.61 min, m/z 564 [MH+]. ¹H NMR (400 MHz, CDCl₃): 1.31 (9H, s), 1.42-1.48 (6H, m), 2.14-2.25 (1H, m), 2.34 (3H, s), 2.82 (1H, dd, J 3.2, 15.3), 3.23 (1H, q, J 6.4) 5.56-5.71 (3H, m), 6.27 (1H, s), 6.62 (1H, s), 7.05 (1H, d, J 9.7), 7.15-7.22 (2H, m), 7.23-7.45 (7H, m), 7.56 (1H, d, 10.5).

EXAMPLE 14

1-(5-tert-Butyl-2-p-tolyl-2H-pyrazol-3-yl)-3-[(1R,3S)-3-(3-isopropyl-[1,2,4]-triazolo[4,3-a]pyridin-6-yloxy)-indan-1-yl]-urea

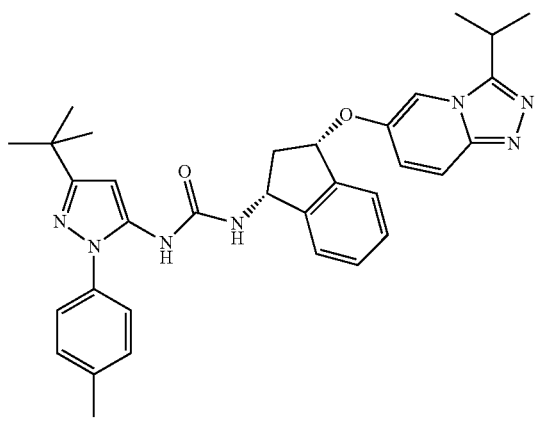 [SMILES: Cc1ccc(-n2nc(C(C)(C)C)cc2NC(=O)N[C@@H]2C[C@H](Oc3ccc4nnc(C(C)C)n4c3)c3ccccc32)cc1]

The title compound was prepared using (1S,3R)-3-amino-indan-1-ol in a similar manner to Example 12. LCMS (Method 5): Rt 4.68 min, m/z 564 [MH+]. ¹H NMR (400 MHz, CDCl₃): 1.29 (9H, s), 1.36-1.45 (6H, m), 1.92-2.00 (1H, m), 2.26 (3H, s), 3.03-3.14 (1H, m), 3.24 (1H, q, J 6.8), 5.33-5.45 (1H, m), 5.49-5.46 (1H, m), 5.94-6.01 (1H, m), 6.25 (1H, s), 6.90 (1H, br s), 6.96-7.01 (1H, m), 7.09 (2H, d, J 7.8), 7.25-7.42 (7H, m), 7.51 (1H, d, J 9.3).

EXAMPLE 15

1-(5-tert-Butyl-2-p-tolyl-2H-pyrazol-3-yl)-3-[(1S,3R)-3-(3-isopropyl-[1,2,4]triazolo[4,3-a]pyridin-6-yloxy)-indan-1-yl]-urea

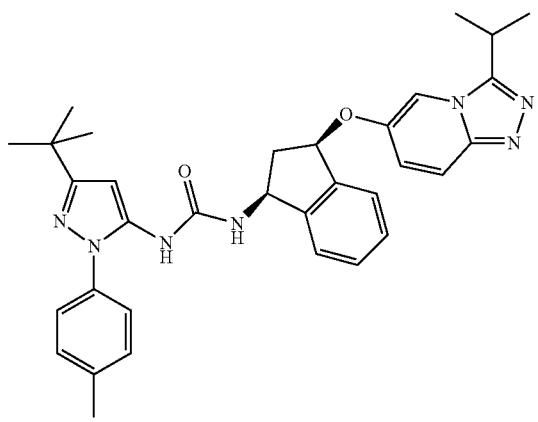 [SMILES: Cc1ccc(-n2nc(C(C)(C)C)cc2NC(=O)N[C@H]2C[C@@H](Oc3ccc4nnc(C(C)C)n4c3)c3ccccc32)cc1]

The title compound was prepared using (1R,3S)-3-amino-indan-1-ol in a similar manner to Example 12. LCMS (Method 5): Rt 4.68 min, m/z 564 [MH+]. ¹H NMR (400 MHz, CDCl₃): 1.29 (9H, s), 1.36-1.45 (6H, m), 1.92-2.00 (1H, m), 2.26 (3H, s), 3.03-3.14 (1H, m), 3.24 (1H, q, J 6.8), 5.33-5.45 (1H, m), 5.49-5.46 (1H, m), 5.94-6.01 (1H, m), 6.25 (1H, s), 6.90 (1H, br s), 6.96-7.01 (1H, m), 7.09 (2H, d, J 7.8), 7.25-7.42 (7H, m), 7.51 (1H, d, J 9.3).

EXAMPLE 16

1-(5-tert-Butyl-isoxazol-3-yl)-3-[(1S,4S)-4-(3-isopropyl-[1,2,4]-triazolo[4,3-a]pyridin-6-yloxy)-1,2,3,4-tetrahydro-naphthalen-1-yl]-urea

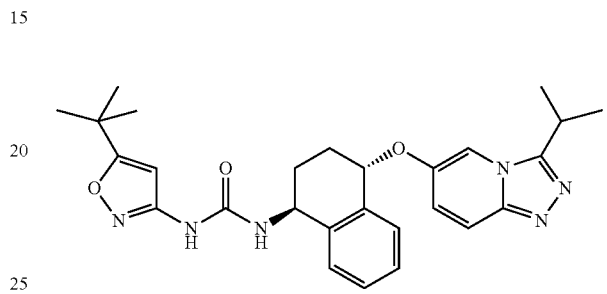

The title compound was prepared in a similar manner to Example 1 steps e and f starting from the product of Example 2 step b and (5-tert-butyl-isoxazol-3-yl)-carbamic acid 2,2,2-trichloro-ethyl ester (WO2006091671). LCMS (Method 5): Rt 4.36 min, m/z 489 [MH+]. ¹H NMR (400 MHz, d₄-MeOH): 1.27 (9 H, s), 1.39 (6H, t, J 6.65), 1.81-1.82 (1 H, m), 2.06 (1 H, m), 2.19 (2 H, m), 3.53-3.62 (1 H, m), 4.99 (1 H, s), 5.63 (1 H, s), 6.38 (1 H, s), 6.96 (1 H, d, J 8.22), 7.23 (1 H, dd, J 9.86 and 2.09), 7.34-7.35 (3 H, m), 7.43 (1 H, d, J 7.45), 7.69 (1 H, dd, J 9.85 and 0.79), 8.24 (1 H, d, J 2.02), 9.24 (1 H, s).

EXAMPLE 17

N-(5-tert-Butyl-3-{3-[(1S,4S)-4-(3-isopropyl-[1,2,4]triazolo[4,3-a]pyridin-6-yloxy)-1,2,3,4-tetrahydro-naphthalen-1-yl]-ureido}-2-methoxy-phenyl)-methanesulfonamide

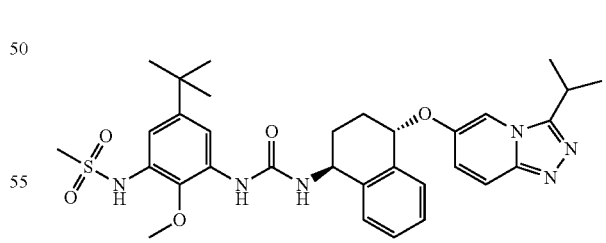

The title compound was prepared in a similar manner to Example 1 steps e and f starting from the product of Example 2 step b and (5-tert-butyl-3-methanesulfonylamino-2-methoxy-phenyl)-carbamic acid 2,2,2-trichloro-ethyl ester. LCMS (Method 5): Rt 4.31 min, m/z 621 [MH+]. ¹H NMR (400 MHz, d₄-MeOH): 1.31 (9 H, s), 1.47 (6 H, dd, J 12.55 and 6.88), 1.92-1.93 (1 H, m), 2.29-2.31 (3 H, m), 3.03 (3 H, s), 3.50-3.59 (1 H, m), 3.75 (3 H, s), 5.12 (1 H, m), 5.58 (1 H, m), 7.16 (1 H, d, J 2.30), 7.33-7.34 (4 H, m), 7.45 (1 H, d, J 7.68), 7.66 (1 H, dd, J 9.90 and 0.81), 8.00 (1 H, d, J 2.31), 8.05 (1 H, d, J 1.98).

EXAMPLE 18

(+/−) 1-(5-tert-Butyl-2-p-tolyl-2H-pyrazol-3-yl)-3-[9-(3-isopropyl-[1,2,4]triazolo[4,3-a]pyridin-6-yloxy)-cis-6,7,8,9-tetrahydro-5H-benzocyclohepten-5-yl]-urea

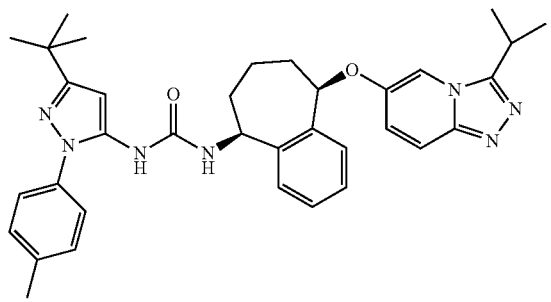 [SMILES: Cc1ccc(-n2nc(C(C)(C)C)cc2NC(=O)N[C@H]2CCC[C@@H](Oc3ccc4nnc(C(C)C)n4c3)c3ccccc32)cc1]

a. (+/−) Cis-9-amino-6,7,8,9-tetrahydro-5H-benzocyclohepten-5-ol

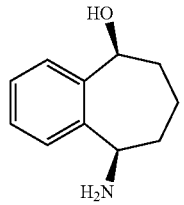

The title compound was prepared in a similar manner to Example 1 steps a and b using 9-azido-6,7,8,9-tetrahydrobenzocyclohepten-5-one. Diastereoisomers were separated by FCC and regioisomers were assigned following NOE(SY) analysis. LCMS (Method 3): Rt 1.44 min, m/z 178 [MH$^+$]. $^1$H NMR (400 MHz, CDCl$_3$): 1.69-1.70 (3 H, m), 2.06-2.07 (1 H, m), 2.18-2.19 (1 H, m), 2.49-2.51 (1 H, m), 4.26 (1 H, dd, J 5.97 and 1.56), 4.68 (1 H, d, J 6.36), 7.15-7.22 (3 H, m), 7.29 (1 H, d, J 7.19).

b. (+/−) 1-(5-tert-Butyl-2-p-tolyl-2H-pyrazol-3-yl)-3-[9-(3-isopropyl-[1,2,4]triazolo[4,3-a]pyridin-6-yloxy)-cis-6,7,8,9-tetrahydro-5H-benzocyclohepten-5-yl]-urea The title compound was prepared in a similar manner to Example 1 steps e and f starting from the product of Example 18 step a. LCMS (Method 5): Rt 4.84 min, m/z 592 [MH$^+$]. $^1$H NMR (400 MHz, d$_6$-DMSO): 1.24 (12 H, m), 1.34 (3H, d, J 6.82), 1.4-2.2 (6 H, m), 2.36 (3 H, s), 3.43 (1 H, m), 5.03-5.08 (1 H, m), 5.71 (1 H, m), 6.26 (1 H, s), 7.11 (1 H, m), 7.21-7.39 (8 H, m), 7.44-7.48 (1 H, m), 7.67 (1 H, d, J 9.83), 7.91 (1 H, s), 8.34 (1 H, br s).

EXAMPLE 19

(+/−) 1-(5-tert-Butyl-2-p-tolyl-2H-pyrazol-3-yl)-3-[9-(3-isopropyl-[1,2,4]triazolo[4,3-a]pyridin-6-yloxy)-trans-6,7,8,9-tetrahydro-5H-benzocyclohepten-5-yl]-urea

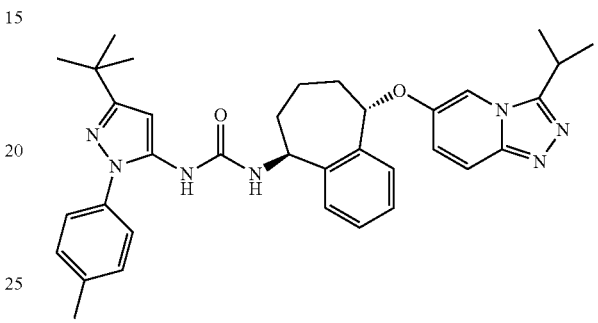

a. (+/−) Trans-9-amino-6,7,8,9-tetrahydro-5H-benzocyclohepten-5-ol

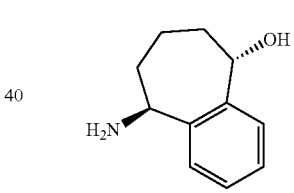

The title compound was prepared in a similar manner to Example 1 steps a and b using 9-azido-6,7,8,9-tetrahydrobenzocyclohepten-5-one. Diastereoisomers were separated by FCC and regioisomers were assigned following NOE(SY) analysis. LCMS (Method 3): Rt 0.81 min, m/z 178 [MH$^+$]. $^1$H NMR (400 MHz, CDCl$_3$): 1.57-2.14 (6 H, m), 4.51 (1 H, m), 5.12 (1 H, m), 7.21-7.22 (2 H, m), 7.36 (2 H, m).

b. (+/−)-1-(5-tert-Butyl-2-p-tolyl-2H-pyrazol-3-yl)-3-[9-(3-isopropyl-[1,2,4]triazolo[4,3-a]pyridin-6-yloxy)-trans-6,7,8,9-tetrahydro-5H-benzocyclohepten-5-yl]-urea The title compound was prepared in a similar manner to Example 1 steps e and f starting from Example 19 step a. LCMS (Method 5): Rt 4.87 min, m/z 592 [MH$^+$]. $^1$H NMR (400 MHz, d$_6$-DMSO): 1.11 (3H, d, J 6.82), 1.17 (3 H, d, J 6.84), 1.21 (9 H, s), 1.69-1.71 (4 H, m), 2.24 (2 H, m), 2.33 (3

H, s), 3.31 (1 H, m), 5.47 (2 H, m), 6.24 (1 H, s), 7.02-7.03 (1 H, m), 7.09-7.24 (4 H, m), 7.30-7.32 (5 H, (1 H, d, J 9.87), 7.98 (1 H, s), 8.18 (1 H, s).

EXAMPLE 20

1-(5-tert-Butyl-2-p-tolyl-2H-pyrazol-3-yl)-3-((1S,4S)-4-{3-[2-(2-hydroxy-ethylsulfanyl)-phenyl]-[1,2,4]triazolo[4,3-a]pyridin-6-yloxy}-1,2,3,4-tetrahydro-naphthalen-1-yl)-urea

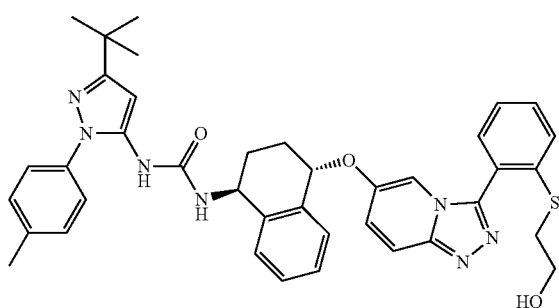 [SMILES: Cc1ccc(-n2nc(C(C)(C)C)cc2NC(=O)N[C@H]2CC[C@H](Oc3ccc4nnc(-c5ccccc5SCCO)n4c3)c3ccccc32)cc1]

a. 6-Fluoro-3-{2-[2-(tetrahydro-pyran-2-yloxy)-ethylsulfanyl]-phenyl}-[1,2,4]-triazolo[4,3-a]pyridine

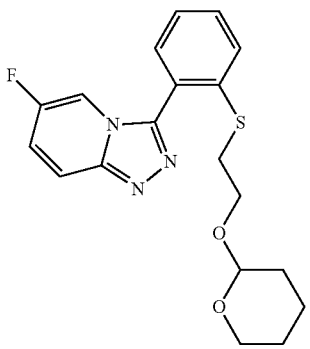 [SMILES: Fc1ccc2nnc(-c3ccccc3SCCOC3CCCCO3)n2c1]

A solution of 2-[2-(6-fluoro-[1,2,4]triazolo[4,3-a]pyridin-3-yl)-phenylsulfanyl]-ethanol (400 mg, 1.38 mmol), 4-methylbenzenesulfonic acid (65 mg, 0.345 mmol) and 3,4-dihydro-2H-pyran (251 µL, 2.76 mmol) in DCM (5 mL) was stirred at RT under a nitrogen atmosphere for 36 h. The reaction mixture was diluted with DCM and extracted with sat. NaHCO$_3$. The organic layer was dried over MgSO$_4$, filtered and concentrated in vacuo. The residue was purified by FCC using MeOH in DCM (0 to 5%) to give the title compound as a pale yellow oil (381 mg, 74%). LCMS (Method 3): Rt 3.10 min, m/z 374 [MH$^+$]. $^1$H NMR (400 MHz, CDCl$_3$): 1.49 (6 H, m), 3.01-3.02 (2 H, m), 3.42-3.59 (2 H, m), 3.80-3.80 (2 H, m), 4.52 (1 H, m), 7.34-7.35 (2 H, m), 7.55-7.55 (2 H, m), 7.67-7.68 (2 H, m), 7.90 (1 H, dd, J 9.97 and 4.82).

b. (1S,4S)-4-(3-{2-[2-(Tetrahydro-pyran-2-yloxy)-ethylsulfanyl]-phenyl}-[1,2,4]triazolo[4,3-a]pyridin-6-yloxy)-1,2,3,4-tetrahydro-naphthalen-1-ylamine

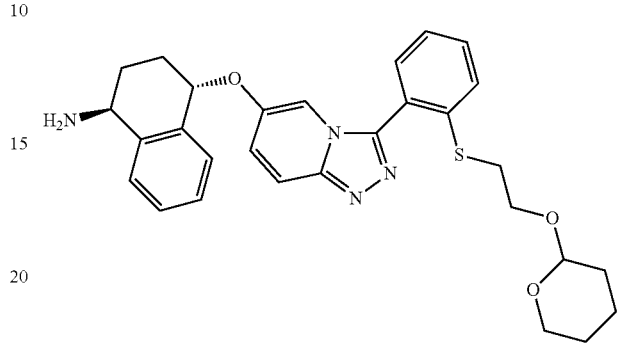

A solution of Example 20 step a (381 mg, 1.02 mmol), Example 2 step b (183 mg, 1.12 mmol), potassium tert-butoxide (125 mg, 1.12 mmol) and DMPU (492 µL, 4.08 mmol) was heated at 50° C. for 2 h then at 80° C. for 1.5 h. The reaction mixture was cooled to RT and partitioned between H$_2$O-EtOAc. The organic layer was dried over MgSO$_4$, filtered and concentrated in vacuo. The residue was purified by FCC using 2M NH$_3$-MeOH in DCM (0 to 50%) to give the title compound (146 mg, 28%). LCMS (Method 3): Rt 2.29 min, m/z 517 [MH$^+$].

c. 1-(5-tert-Butyl-2-p-tolyl-2H-pyrazol-3-yl)-3-[(1S,4S)-4-(3-{2-[2-(tetrahydro-pyran-2-yloxy)-ethylsulfanyl]-phenyl}-[1,2,4]triazolo[4,3-a]pyridin-6-yloxy)-1,2,3,4-tetrahydro-naphthalen-1-yl]-urea

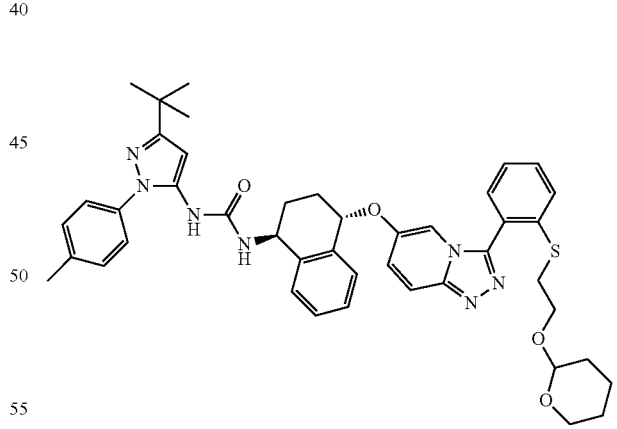

A solution of Example 20 step b (60 mg, 0.11 mmol), DIPEA (26 µL, 0.15 mmol) and 2,2,2-trichloroethyl 3-tert-butyl-1-p-tolyl-1H-pyrazol-5-ylcarbamate (56 mg, 0.138 mmol) in dioxane (5 mL) was heated at 80° C. for 20 h. The reaction was allowed to cool to RT, partitioned between H$_2$O-DCM, the organic phase dried (MgSO$_4$) and concentrated in vacuo. The residue was purified by FCC using MeOH in DCM (0 to 5%) to give the title compound as a yellow foam (38 mg, 45%). LCMS (Method 3): Rt 4.09 min, m/z 772 [MH$^+$].

d. 1-(5-tert-Butyl-2-p-tolyl-2H-pyrazol-3-yl)-3-((1S, 4S)-4-{3-[2-(2-hydroxy-thylsulfanyl)-phenyl]-[1,2,4]triazolo[4,3-a]pyridin-6-yloxy}-1,2,3,4-tetrahydro-naphthalen-1-yl)-urea A solution of Example 20 step c (38 mg, 0.05 mmol) and 4-methylbenzenesulfonic acid (9 mg, 0.05 mmol) in MeOH (2 mL) was stirred at RT for 3 h then at 60° C. for 5 h. The mixture was cooled to RT and concentrated in vacuo. The residue was purified by FCC using MeOH in DCM (0 to 10%) to give the title compound as a yellow solid (15 mg, 44%). LCMS (Method 5): Rt 4.83 min, m/z 688 [MH+]. $^1$H NMR (400 MHz, d$_6$-DMSO): 1.26 (9 H, s), 1.69 (1 H, m), 2.00-2.11 (3 H, m), 2.35 (3 H, s), 3.01 (2 H, t, J 6.60), 3.50 (2 H, t, J 6.60), 4.87 (1 H, m), 5.55 (1 H, m), 6.32 (1 H, s), 6.98 (1 H, d, J 8.10), 7.11 (4 H, d, J 7.86), 7.31-7.33 (5 H, m), 7.47 (4 H, m), 7.63-7.71 (1 H, m), 7.79 (1 H, s), 7.96 (1 H, d, J 3.40).

EXAMPLE 21

1-(5-tert-Butyl-2-p-tolyl-2H-pyrazol-3-yl)-3-[(1S, 4S)-4-(3-tert-butyl[1,2,4]triazolo[4,3a]pyridin-6-yloxy)-1,2,3,4-tetrahydro-naphthalen-1-yl]-urea

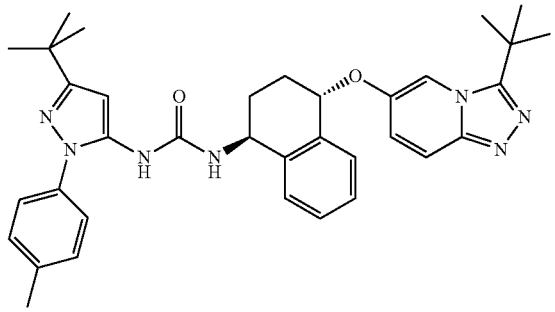 [SMILES: Cc1ccc(-n2nc(C(C)(C)C)cc2NC(=O)N[C@H]2CC[C@H](Oc3ccc4nnc(C(C)(C)C)n4c3)c3ccccc32)cc1]

The title compound was prepared in a similar manner to Example 2. LCMS (Method 5): Rt 4.86 min, m/z 592 [MH+]. $^1$H NMR (400 MHz, d$_4$-MeOH): 1.29 (9H, s), 1.50 (9H, s), 1.72-1.80 (1H, m), 2.11-2.19 (2H, s), 2.22-2.29 (1H, s), 2.37 (3H, s), 4.99 (1H, t, J 4), 5.46 (1H, t, J 4), 6.32 (1H, s), 7.18-7.34 (10H, m), 7.63-7.65 (1H, m), 7.93 (1H, s).

EXAMPLE 22

N-(4-{(1S,4S)-4-[3-(5-tert-Butyl-2-p-tolyl-2H-pyrazol-3-yl)-ureido]-1,2,3,4-tetrahydro-naphthalen-1-yloxymethyl}-pyridin-2-yl)-2-methoxy-acetamide

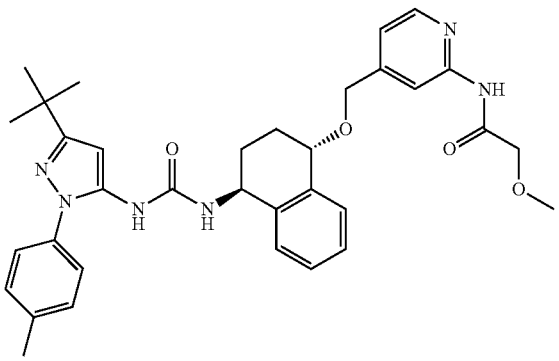 [SMILES: COCC(=O)Nc1cc(CO[C@H]2CC[C@H](NC(=O)Nc3cc(C(C)(C)C)nn3-c3ccc(C)cc3)c3ccccc32)ccn1]

a. ((1S,4S)-4-Hydroxy-1,2,3,4-tetrahydro-naphthalen-1-yl)-carbamic acid tert-butyl ester

A solution of Example 2 step b (0.47 g, 2.9 mmol) and di-tert-butyl dicarbonate (0.7 g, 3.19 mmol) in acetonitrile (10 mL) was stirred at RT for 20 h. The solvents were removed in vacuo and the residue was purified by FCC using EtOAc in cyclohexane (0 to 40%) to afford the title compound as a pink solid (0.56 g, 74%). $^1$H NMR (400 MHz, d6-DMSO): 1.41 (9 H, s), 1.62 (2 H, m), 1.95-2.14 (2 H, m), 4.54 (1 H, m), 4.66 (1 H, m), 5.18 (1 H, d, J 6.29), 7.18-7.19 (3 H, m), 7.41-7.43 (1 H, m).

b. [(1S,4S)-4-(2-Amino-pyridin-4-ylmethoxy)-1,2,3,4-tetrahydro-naphthalen-1-yl]-carbamic acid tert-butyl ester

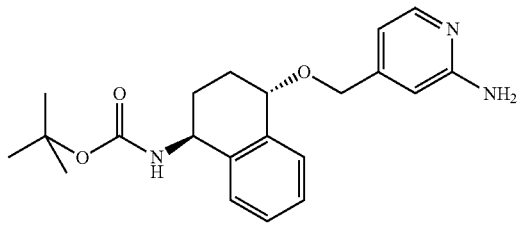 [SMILES: CC(C)(C)OC(=O)N[C@H]1CC[C@H](OCc2ccnc(N)c2)c2ccccc21]

A solution of Example 21 step a (240 mg, 0.912 mmol) in DMF (5 mL), cooled to 0° C., was treated with sodium hyrdide (70 mg, 1.82 mmol) and 4-bromomethyl-pyridine-2-yl amine hydrobromide salt (249 mg, 0.93 mmol). The reaction mixture was stirred at 0° C. for 1 h then allowed to warm to RT. The solvent was reduced in vacuo and the residue purified by FCC using EtOAc in DCM (0 to 100%) to give the title compound as a brown gum (145 mg, 43%). LCMS (Method 3): Rt 2.47 min, m/z 370 [MH+]. $^1$H NMR (400 MHz, d6-DMSO): 1.43 (9 H, s), 1.62-1.64 (1 H, m), 1.80-1.82 (1 H, m), 2.08 (1 H, m), 2.16-2.25 (1H, m), 4.46-4.49 (3 H, m), 4.72 (1 H, m), 5.86 (2 H, br s), 6.44-6.45 (2 H, m), 7.19-7.27 (3 H, m), 7.37-7.38 (1 H, m), 7.84 (1 H, d, J 5.16).

c. 4-((1S,4S)-4-Amino-1,2,3,4-tetrahydro-naphthalen-1-yloxymethyl)-pyridin-2-ylamine

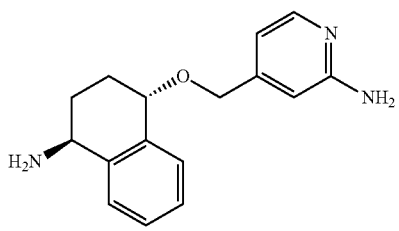 [SMILES: Nc1cc(CO[C@H]2CC[C@H](N)c3ccccc32)ccn1]

A solution of Example 21 step b (130 mg, 0.35 mmol) and TFA (1 mL) in DCM (5 mL) was stirred at RT for 2 h and concentrated in vacuo to give the title compound as an orange gum (68 mg, 72%). LCMS (Method 3): Rt 0.31 min, m/z 270 [MH+].

d. 1-[(1S,4S)-4-(2-Amino-pyridin-4-ylmethoxy)-1,2,3,4-tetrahydro-naphthalen-1-yl]-3-(5-tert-butyl-2-p-tolyl-2H-pyrazol-3-yl)-urea

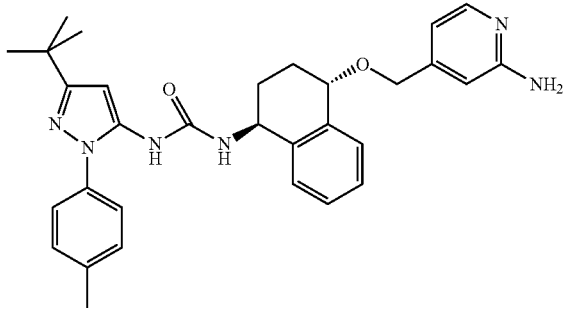 [SMILES: Cc1ccc(-n2nc(C(C)(C)C)cc2NC(=O)N[C@H]2CC[C@H](OCc3ccnc(N)c3)c3ccccc32)cc1]

The title compound was prepared in a similar manner to Example 20 steps c starting from the product of Example 21 step c. LCMS (Method 3): Rt 2.64 min, m/z 525 [MH+].

e. N-(4-{(1S,4S)-4-[3-(5-tert-Butyl-2-p-tolyl-2H-pyrazol-3-yl)-ureido]-1,2,3,4-tetrahydro-naphthalen-1-yloxymethyl}-pyridin-2-yl)-2-methoxy-acetamide A solution of Example 21 step d (40 mg, 0.076 mmol), DIPEA (28 μL, 0.167 mmol) and methoxyacetyl chloride (15.2 μL, 0.16 mmol) in DCM (1 mL) was stirred at RT for 2 h. The reaction mixture was concentrated in vacuo and the residue purified by HPLC (30 to 95% CH$_3$CN in H2O+0.1% formic acid) to give the title compound as a white solid (21 mg, 46%). LCMS (Method 5): Rt 5.05 min, m/z 597 [MH+]. $^1$H NMR (400 MHz, d6-DMSO): 1.26 (9 H, s), 1.62-1.68 (1 H, m), 2.05-2.07 (3 H, m), 2.35 (3 H, s), 3.36 (3 H, s), 4.05 (2 H, s), 4.63-4.64 (3 H, m), 4.84 (1 H, m), 6.31 (1 H, s), 6.96 (1 H, d, J 8.33), 7.10 (1 H, d, J 5.15), 7.28-7.29 (7 H, m), 7.40-7.44 (1 H, m), 7.98 (1 H, s), 8.11 (1 H, s), 8.26 (1H, d, J 5.10), 9.93 (1 H, s).

Biological Assays
p38 Kinase Assay

Human recombinant p38 enzyme expressed in *E. coli* and activated by incubation with MKK6 enzyme (Calbiochem #559324) is used as source of enzyme activity.

The assay is carried in high binding, clear, flat bottom 96 well assay plates which have been coated with recombinant ATF-2 (Biosource #PHF0043). Test compounds are incubated with p38 kinase for 2h prior to initiating the kinase assay by the addition of ATP to obtain an assay concentration of 250 μM. Phosphorylation of ATF-2 is detected and quantified using an ELISA. This consists of sequential incubation in the presence of anti-phospho-ATF2, biotinylated anti-IgG and streptavidin-HRP. Incubation with an HRP chromogenic substrate (TMB) results in absorbance that is proportional to the amount of phosphorylated substrate produced. Absorbance is detected using a multiwell plate reader.

Compounds are diluted in DMSO prior to addition to assay buffer, the final DMSO concentration in the assay being 1%.

The IC$_{50}$ is defined as the concentration at which a given compound achieves 50% inhibition of control.

Results are shown in the following Table:

TABLE 1

| Example | p38α inhibition |
|---|---|
| Example 1 | ++++ |
| Example 2 | ++++ |
| Example 3 | ++++ |
| Example 4 | ++++ |
| Example 5 | +++ |
| Example 6 | ++++ |
| Example 7 | ++++ |
| Example 8 | ++ |
| Example 9 | ++ |
| Example 10 | ++++ |
| Example 11 | ++++ |
| Example 12 | ++ |
| Example 13 | ++++ |
| Example 14 | + |
| Example 15 | + |
| Example 16 | ++++ |
| Example 17 | ++++ |
| Example 18 | +++ |
| Example 19 | +++ |
| Example 20 | ++++ |
| Example 21 | NT |
| Example 22 | ++++ |

In the table above, p38α binding potencies (IC$_{50}$ values) are indicated as follows: <7000-500 nM '+'; <500-100 nM '++'; 10-<100 nM '+++'; <10 nM '++++'.
All compounds tested exhibited IC$_{50}$ values <7000 nM. NT not tested.

p38 Functional Assay

Inhibition of cellular p38 depresses the release of TNFα, a functional response which is quantified by measurement of the amount of TNFα in the supernatants of LPS activated THP-1 cells (an immortalised monocytic cell line) or peripheral blood mononuclear cells (PBMC's) isolated from freshly drawn human blood.

Cells seeded in 96 well plates are pre-treated by the addition of p38 inhibitors for 1h followed by addition of lipopolysaccharide (LPS) to activate cytokine production and release. The amount of TNFα released into the cell supernatants is quantified using an R&D Systems enzyme linked immunosorbant assay (ELISA) kit (product DY210) following the manufacturers instructions.

Compounds are diluted in DMSO prior to addition, the final DMSO concentration in the assay being 0.3%. The EC$_{50}$ is defined as the concentration at which a given compound achieves 50% inhibition of the control. Results for tested compounds are shown in Table 2:

TABLE 2

| Example | EC$_{50}$ (THP-1) |
|---|---|
| Example 1 | ++++ |
| Example 2 | ++++ |
| Example 3 | ++++ |
| Example 4 | ++++ |
| Example 6 | ++++ |
| Example 7 | ++++ |
| Example 10 | ++++ |
| Example 11 | ++++ |

In Table 2 above, EC$_{50}$ values are indicated as follows: <7000-500 nM '+'; <500-100 nM '++'; 10-<100 nM '+++'; <10 nM '++++'.
All compounds tested exhibited EC$_{50}$ values <2000 nM.

The invention claimed is:

1. A compound of formula (I), or a pharmaceutically acceptable salt thereof:

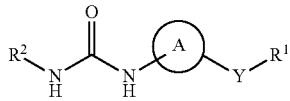
(I)

wherein;

R¹ is a radical of formula (IB):

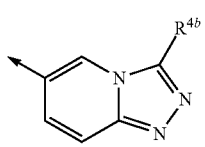
(IB)

wherein
R$^{4b}$ is C$_1$-C$_6$ alkyl, C$_3$-C$_6$ cycloalkyl, phenyl which is optionally substituted with at least one substituent selected from the group consisting of halo, —O-benzyl, hydroxyl, and hydroxyl(C$_1$-C$_6$)alkylthio;

Y is —O—;

A is a divalent radical of formula (Va) in either orientation;

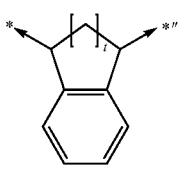
(Va)

wherein t is 1, 2, or 3;
R² is a radical of formula (IIIa), (IIIb), or (IIIc):

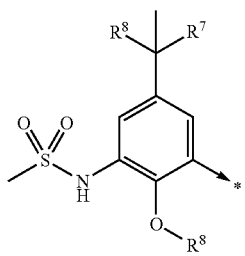
(IIIa)

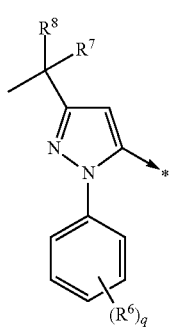
(IIIb)

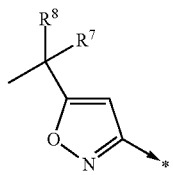
(IIIc)

wherein
q is 0, 1, 2 or 3;
R⁷ is —CH$_3$; —C$_2$H$_5$; —CH$_2$OH, —CH$_2$SCH$_3$; —SCH$_3$ or —SC$_2$H$_5$;
R⁸ is —CH$_3$ or —C$_2$H$_5$; and
each occurrence of R⁶ is independently H, C$_1$—C$_6$ alkyl, hydroxy or halo.

2. A compound or pharmaceutically acceptable salt thereof according to claim 1, wherein -NH-A-Y- is a divalent radical having one of the stereospecific formulae (B), (C), (D), (E), (F), (G), (H), (I) or (J), wherein Y is as defined with reference to formula (I):

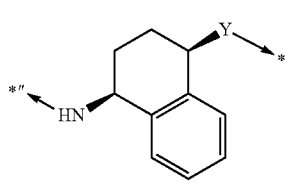
(B)

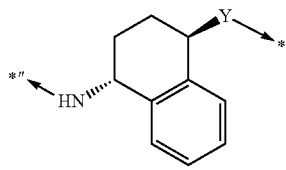
(C)

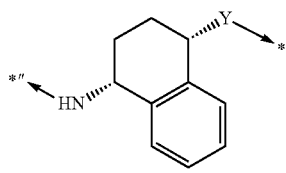
(D)

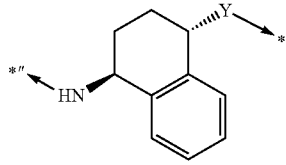
(E)

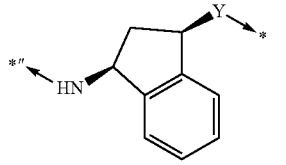
(F)

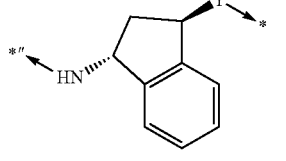
(G)

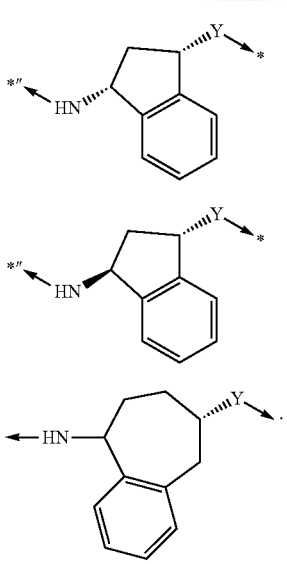

3. A compound or pharmaceutically acceptable salt thereof according to claim 2, wherein -NH-A-Y- has formula (B), (C), (D), (E), (I) or (J).

4. A compound or pharmaceutically acceptable salt thereof according to claim 1, wherein $R^{4b}$ is isopropyl, cyclopentyl, or phenyl which is optionally substituted by one or two groups selected from the group consisting of halogen and hydroxy.

5. A compound or pharmaceutically acceptable salt thereof according to claim 1, wherein $R^{4b}$ is 2,6-dichlorophenyl, 2-chlorophenyl, or 2-hydroxyphenyl.

6. A compound or pharmaceutically acceptable salt thereof according to claim 1, wherein $R^2$ is a group (IIIb) or (IIIc) wherein $R^7$ and $R^8$ are independently ethyl or methyl.

7. A pharmaceutical composition, comprising a compound or pharmaceutically acceptable salt thereof according to claim 1 together with one or more pharmaceutically acceptable carriers.

8. A composition as claimed in claim 7, which is adapted for inhalation for pulmonary administration.

* * * * *